US011553843B2

(12) United States Patent
Ashrafi

(10) Patent No.: US 11,553,843 B2
(45) Date of Patent: Jan. 17, 2023

(54) TOPOLOGICAL FEATURES AND TIME-BANDWIDTH SIGNATURE OF HEART SIGNALS AS BIOMARKERS TO DETECT DETERIORATION OF A HEART

(71) Applicant: NxGen Partners IP, LLC, Dallas, TX (US)

(72) Inventor: Solyman Ashrafi, Plano, TX (US)

(73) Assignee: NXGEN PARTNERS IP, LLC, Dallas, TX (US)

( * ) Notice: Subject to any disclaimer, the term of this patent is extended or adjusted under 35 U.S.C. 154(b) by 498 days.

(21) Appl. No.: 16/748,228

(22) Filed: Jan. 21, 2020

(65) Prior Publication Data
US 2020/0155015 A1 May 21, 2020

Related U.S. Application Data

(63) Continuation-in-part of application No. 16/161,840, filed on Oct. 16, 2018, now Pat. No. 10,755,188.
(Continued)

(51) Int. Cl.
*A61B 5/00* (2006.01)
*A61B 5/02* (2006.01)
(Continued)

(52) U.S. Cl.
CPC ........ *A61B 5/02028* (2013.01); *A61B 5/6802* (2013.01); *A61B 5/746* (2013.01);
(Continued)

(58) Field of Classification Search
CPC ...... A61B 5/6802; A61B 5/7235–7267; A61B 5/7461
See application file for complete search history.

(56) References Cited

U.S. PATENT DOCUMENTS

2008/0139954 A1* 6/2008 Day ..................... A61N 1/3956
600/523
2008/0256009 A1 10/2008 Jiang et al.
(Continued)

OTHER PUBLICATIONS

"Taking an ECG with the ECG App on Apple Watch Series 4 or Later." Apple Support, Mar. 24, 2020, support.apple.com/en-us/HT208955.
(Continued)

*Primary Examiner* — Scott M. Getzow
(74) *Attorney, Agent, or Firm* — Gregory M. Howison

(57) ABSTRACT

A system monitors an individual for conditions indicating a possibility of occurrence of irregular heart events. A database includes a plurality of combinations of at least a first signature and a second signature. A first portion of the plurality of combinations is associated with a normal heartbeat and a second portion of the plurality of combinations is associated with an irregular heart event. A wearable heart monitor that is worn on a body of the patient includes a heart sensor for generating a heart signal responsive to monitoring a beating of a heart of the individual. The monitor further includes a processor for receiving the heart signal from the heart sensor. The processor is configured to analyze the heart signal using a plurality of different processes. Each of the plurality of different processes generates at least one of the first signature and the second signature. The plurality of different processes provide a unique combination including at least the first signature and the second signature for the generated heart signal. The processor compares the unique combination with the plurality of combinations in the database, locates a combination of the plurality of combinations that substantially matches the unique combination and generates a first indication if the unique combination substantially matches one of the first portion of the plurality of
(Continued)

combinations and a second indication if the unique combination substantially matches one of the second portion of the plurality of combinations.

28 Claims, 27 Drawing Sheets

Related U.S. Application Data

(60) Provisional application No. 62/574,039, filed on Oct. 18, 2017.

(51) Int. Cl.
*G06N 3/12* (2006.01)
*G06N 20/00* (2019.01)
*G06F 16/901* (2019.01)
*G06N 3/04* (2006.01)
*G06N 7/08* (2006.01)

(52) U.S. Cl.
CPC ....... *G06F 16/9024* (2019.01); *G06N 3/0445* (2013.01); *G06N 3/126* (2013.01); *G06N 7/08* (2013.01); *G06N 20/00* (2019.01)

(56) References Cited

U.S. PATENT DOCUMENTS

2017/0147722 A1     5/2017  Greenwood
2019/0082988 A1*    3/2019  Datta .................... A61B 5/316
2019/0374160 A1*   12/2019  Yin ...................... A61B 5/14551
2021/0353166 A1*   11/2021  Sirendi ................ A61B 5/0816

OTHER PUBLICATIONS

Byrne R, Constant O, Smyth Y, Callagy G, Nash P, et al . . . (2008) Multiple source surveillance incidence and aetiology of out-of-hospital sudden cardiac death in a rural population in the West of Ireland. Eur Heart J., 29, 1418-1423.
Chugh SS (2001) Sudden cardiac death with apparently normal heart: clinical implications of progress in pathophysiology. Cardiac Electrophysiology Review, 5, 394-402.
Chugh SS, Jui J, Gunson K, Stecker EC, John BT, et al . . . (2004) Current burden of sudden cardiac death: multiple source surveillance versus retrospective death certificate-based review in a large U.S. Community. J Am Coll Cardiol. 44, 1268-1275.
Chugh SS, Kelly KL, Titus JL (2000) Sudden cardiac death with apparently normal heart. Circulation, 102, 649-654.
Chugh SS, Reinier K, Teodorescu C, Evanado A, Kehr E, et al . . . (2008) Epidemiology of sudden cardiac death: clinical and research implications. Prog Cardiovasc Dis. 51, 213-228.
E. Baake et al., "Fitting Ordinary Differential Equations to Chaotic Data," Phys. Rev. A, 45, 1985.
Ebrahimzadeh E, Pooyan M (2011) Early detection of sudden cardiac death by using classical linear techniques and time-frequency methods on electrocardiogram signals. Biomedical Science and Engineering, 11, 699-706.
F. Takens, "Detecting Strange Attractors in Turbulence," In Lecture Notes in Mathematics, vol. 898, 366 Berlin: Springer-Verlag, 1981.
Fishman GI, Chugh SS, Dimarco JP, Albert CM, Anderson ME, et al . . . (2010) Sudden Cardiac Death Prediction and Prevention: Report from a National Heart, Lung, and Blood Institute and Heart Rhythm Society Workshop. Circulation, 122, 2335-2348.
Fox CS, Evans JC, Larson MG, Kannel WB, Levy D (2004) Temporal trends in coronary heart disease mortality and sudden cardiac death from 1950 to 1999: the Framingham Heart Study. Circulation, 110, 522-527.
H. Van Loon and K. Labitzke, "Association Between the 11-Year Solar Cycle, the QBO, and the Atmosphere, Part II," J Climate, 1, 1988.
J.H. Bentley, "Multidimensional Binary Search Trees in Data Base Applications," IEEE Transactions on Software Engineering, 5 (4), 1979.
J.M. Martinerie et al., "Mutual Information, Strange Attractors, and the Optimal Estimation of Dimension," Phys. Rev. A., 45, 1992.
Joo S, Choi KJ, Huh SJ (2012) Prediction of spontaneous ventricular tachyarrhythmia by an artificial neural network using parameters gleaned from short-term heart rate variability. Expert Systems with Applications, 39, 3862-3866.
Lei Zhang, "Artificial Neural Network Model Design and Topology Analysis for FPGA Implementation of Lorenz Chaotic Generator", Apr. 2017, 2017 IEEE 30th Canadian Conference on Electrical and Computer Engineering (CCECE), pp. 1-4. (Year: 2017).
Lloyd-Jones D, Adams RJ, Brown TM, Carnethon M, Dai S, et al. (2010) American Heart Association Statistics Committee and Stroke Statistics Subcommittee. Heart disease and stroke statistics2010 update: a report from the American Heart Association. Circulation 121: e46e215.
Myerburg RJ (2005) Cardiac Arrest and Sudden Cardiac Death in Heart Disease: A Textbook of Cardiovascular Medicine, 7th edition. Philadelphia: WB Saunders.
N. Packard et al., "Geometry From a Time Series," Phys. Rev. Lett., 45, 1980.
Nichol G, Thomas E, Callaway CW, Hedges J, Powell JL, et al . . . (2008) Regional variation in out-of-hospital cardiac arrest incidence and outcome. JAMA. 300, 1423-1431.
S. Ashrafi and L. Roszman, "Evidence of Chaotic Pattern in Solar Flux Through a Reproducible Sequence of Period-Doubling-Type Bifurcations," Proceedings of Flight Mechanics/Estimation Theory Symposium, National Aeronautics and Space Administration, Goddard Space Flight Center, Greenbelt, Maryland, May 1991.
S. Ashrafi and L. Roszman, "Lyapunov Exponent of Solar Flux Time Series," Proceedings of First Experimental Chaos Conference, Jun. 1991.
S. Ashrafi and L. Roszman, "Nonlinear Techniques for Forecasting Solar Activity Directly From its Time Series," Proceedings of Flight Mechanics/Estimation Theory Symposium, National Aeronautics and Space Administration, Goddard Space Flight Center, Greenbelt, Maryland May 21-23, 1992.
S. Ashrafi and L. Roszman, Detecting and Disentangling Nonlinear Structure from Solar Flux Time Series, 43rd Congress of the International Astronautical Federation, Aug. 1992.
S. Ashrafi and L. Roszman, Solar Flux Forecasting Using Mutual Information with Optimal Delay, AAS 93-311, Spaceflight Dynamics 1993, American Astronautical Society Publication, Advances in the Astronautical Sciences, vol. 84 Part II pp. 901-913.
S. Ashrafi, Combining Schatten's Solar Activity Prediction Model With a Chaotic Prediction Model, National Aeronautics and Space Administration, Goddard Space Flight Center, Greenbelt, Maryland, 554-FDD-911125, Nov. 1991.
Madimir Golovko, Yury Savitsky, and Nikolaj Maniakov, "Chapter 6 Neural Networks for Signal Processing in Measurement Analysis and Industrial Applications", 2003, NATO Science Series Sub Series III Computer and Systems Sciences 185, pp. 119-144. (Year: 2003).

\* cited by examiner

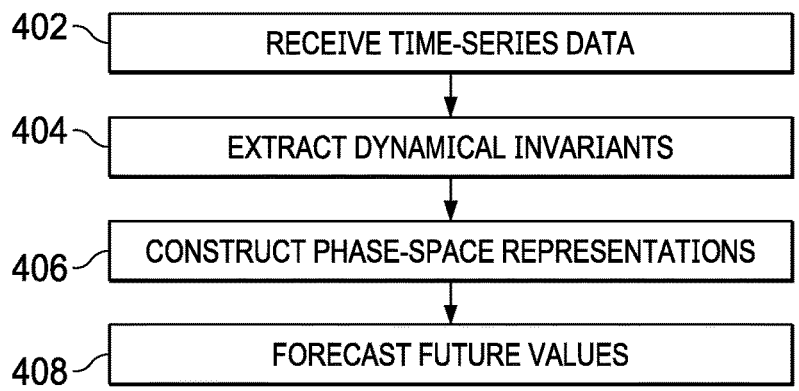
FIG. 4
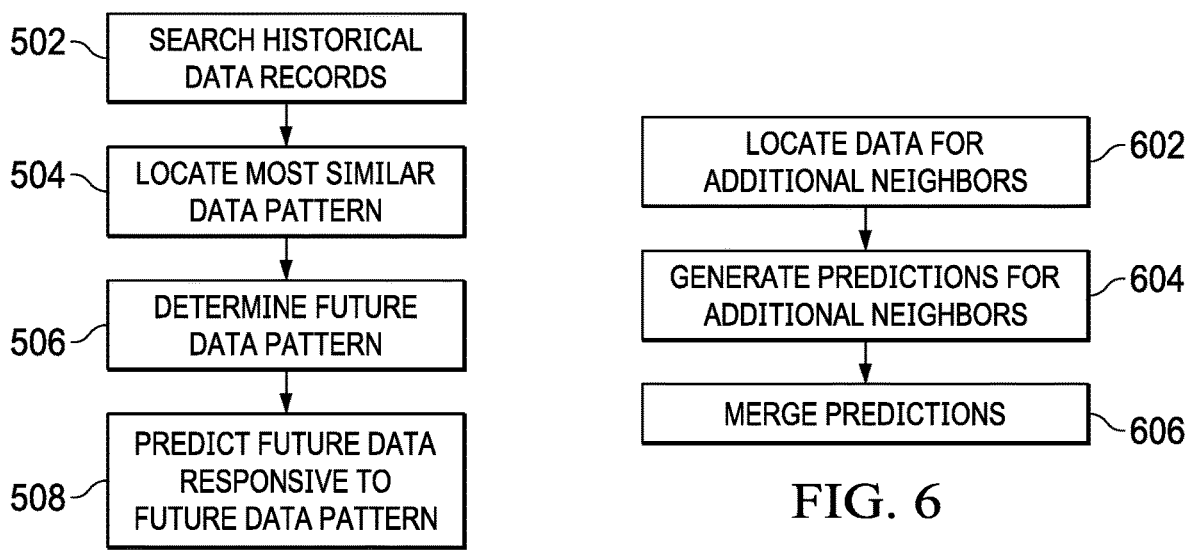
FIG. 5
FIG. 6

TOPOLOGICAL FEATURES AND TIME-BANDWIDTH SIGNATURE OF HEART SIGNALS AS BIOMARKERS TO DETECT DETERIORATION OF A HEART

CROSS-REFERENCE TO RELATED APPLICATIONS

This application is a continuation-in-part of U.S. patent application Ser. No. 16/161,840, entitled A UNIFIED NONLINEAR MODELING APPROACH FOR MACHINE LEARNING AND ARTIFICIAL INTELLIGENCE (ATTRACTOR ASSISTED AI), filed Oct. 16, 2018. U.S. patent application Ser. No. 16/161,840 claims benefit of U.S. Provisional Application No. 62/574,039, filed Oct. 18, 2017, entitled NONLINEAR MODELING AND FORECASTING AND ITS APPLICATION TO ARTIFICIAL INTELLIGENCE, the specification of which is incorporated by reference herein in its entirety.

TECHNICAL FIELD

The present invention relates to heart monitoring systems, and more particularly, to a method for using topological features and time-bandwidth signatures of heart signals to detect heart deterioration.

BACKGROUND

Heart attacks and related types of conditions causing sudden cardiac death (SCD) are a major cause of death among individuals. Currently there exist systems for monitoring an individual's heart signals and generating a real time output of the monitored heart signal. The ability to monitor the heart signals and detect conditions which would potentially indicate an oncoming SCD event would be of great use to the health care industry. Individuals would be able to be warned when their heart signals indicated a potential SCD condition and seek immediate medical attention.

SUMMARY

The present invention, as disclosed and described herein, in one aspect thereof, comprises a system for monitoring an individual for conditions indicating a possibility of occurrence of irregular heart events. A database includes a plurality of combinations of at least a first signature and a second signature. A first portion of the plurality of combinations is associated with a normal heartbeat and a second portion of the plurality of combinations is associated with an irregular heart event. A wearable heart monitor that is worn on a body of the patient includes a heart sensor for generating a heart signal responsive to monitoring a beating of a heart of the individual. The monitor further includes a processor for receiving the heart signal from the heart sensor. The processor is configured to analyze the heart signal using a plurality of different processes. Each of the plurality of different processes generates at least one of the first signature and the second signature. The plurality of different processes provide a unique combination including at least the first signature and the second signature for the generated heart signal. The processor compares the unique combination with the plurality of combinations in the database, locates a combination of the plurality of combinations that substantially matches the unique combination and generates a first indication if the unique combination substantially matches one of the first portion of the plurality of combinations and a second indication if the unique combination substantially matches one of the second portion of the plurality of combinations.

BRIEF DESCRIPTION OF THE DRAWINGS

For a more complete understanding, reference is now made to the following description taken in conjunction with the accompanying Drawings in which:

FIG. 4 illustrates a flow diagram of a process enabling AI systems to forecast future values based upon past time-series data;

FIG. 5 illustrates a flow diagram of a process for predicting future data from historical data records;

FIG. 6 illustrates a flow diagram of a process for merging predictions from nearest neighbor approximations;

DETAILED DESCRIPTION

Figure 1:
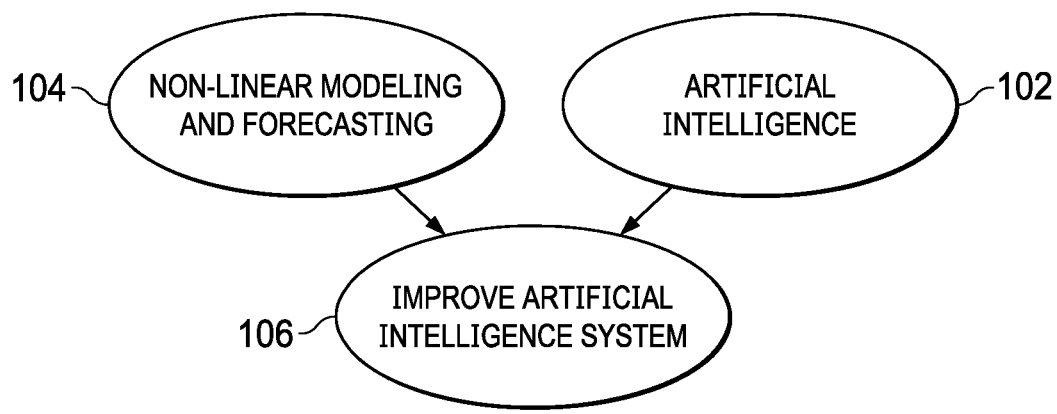
FIG. 1 illustrates a combination of nonlinear modeling and forecasting with an artificial intelligence system.

Referring now to the drawings, wherein like reference numbers are used herein to designate like elements throughout, the various views and embodiments of a system for using topological features and time bandwidth signature of heart signals as biomarkers to detect deterioration of a heart are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Figure 2:
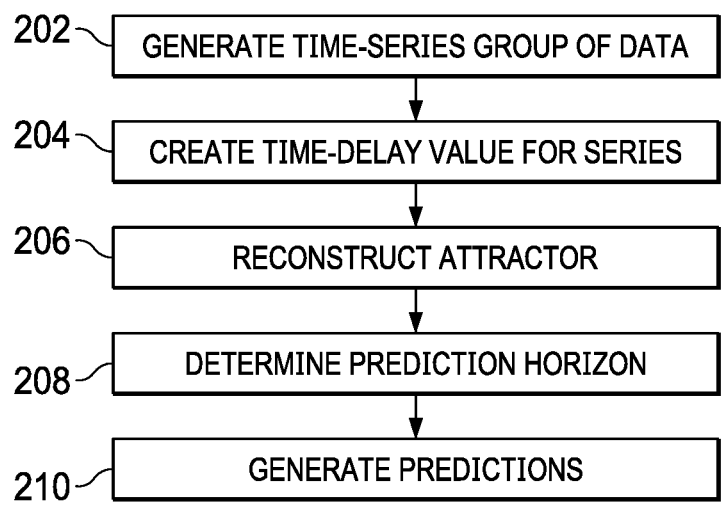
FIG. 2 illustrates a flow diagram of the process for nonlinear modeling and forecasting.

Referring now to the drawings, and more particularly to FIG. 1, there is illustrated the manner in which an artificial intelligence system 102 may be combined with a process for nonlinear modeling and forecasting 104 as described herein to provide an improved artificial intelligence system 106. FIG. 2 is a flow diagram illustrating the general process for nonlinear modeling and forecasting 104 that can be implemented within an artificial intelligence system 102. Initially, with respect to a group of data being analyzed, a time series group of the data is generated at step 202. A time series is a series of data points indexed in time order. Most commonly, a time series is a sequence taken at successive equally spaced points in time. Thus, it is a sequence of discrete-time data. Time series data has a natural temporal progression. Next, a delay value for the time series is created at step 204. Based upon the time series group of data and the created the attractor is reconstructed at step 206. A prediction horizon for the data set is determined at step 208.

An attractor is a set of numerical values toward which a system tends to evolve, for a wide variety of starting conditions of the system. System values that come close enough to the attractor values remain close even if slightly disturbed. In finite-dimensional systems, evolving variable may be represented algebraically as an n-dimensional vector. The attractor is a region in n-dimensional space in physical systems; the n-dimensions may be, for example, two or three positional coordinates for each one or more physical entity. If the evolving variable is two or three dimensional, the attractor of the dynamic process can be represented geometrically in two or three dimensions. An attractor can be a point, a finite set of points, a curve, a manifold or even a complicated set with a fractal structure known as a strange attractor. Describing the attractors of chaotic dynamical systems may be done in Chaos Theory.

A dynamical system is a system in which a function describes the time dependence of a point in a geometric space. Examples include the mathematical models describing the swinging of a clock pendulum, the flow of water in a pipe and the number of fish each spring in a lake. At any given time, a dynamical system has a state even by a tuple of real numbers (a vector) that can be represented by a point in an appropriate state space (a geometrical manifold). The evolution rule of the dynamical system is a function that describes what future states follow from the current state. Often the function is deterministic, that is, for a given time interval one future state follows from the current state. However, some systems are stochastic, in that random events also affect the evolution of the state variables. A trajectory of the dynamical system in the attractor does not have to satisfy any special constraints except for remaining on the attractor, forwarding time. This enables the attractor to be utilized for predictions. The trajectory may be periodic or chaotic. If a set of points is periodic or chaotic, with the flow in the neighborhood is away from the set, the set is not an attractor but instead called a repeller. From the attractor various predictions may be generated at step 210 in order to predict future behavior based upon the provided time series data. The process for nonlinear modeling and forecasting 104 utilized herein is more particularly described hereinbelow.

In the past, the modeling and forecasting of time series data that had nonlinear structure involved attempts to model the systems underlying physics. For example highly entangled dynamics in solar activity data was uncovered as disclosed in S. Ashrafi and L. Roszman, *Detecting and Disentangling Nonlinear Structure from Solar Flux Time Series,* 43rd Congress of the International Astronautical Federation, August 1992, which is incorporated herein by reference. This disclosure discovered that the general lack of predictability in solar activity data arises from its nonlinear nature as more fully discussed in S. Ashrafi and L. Roszman, "Evidence of Chaotic Pattern in SolarFlux Through a Reproducible Sequence of Period-Doubling-Type Bifurcations," *Proceedings of Flight]Mechanics/Estimation Theory Symposium,* National Aeronautics and Space Administration, Goddard Space Flight Center, Greenbelt, Md., May 1991 and S. Ashrafi, *Combining Schatten's Solar Activity Prediction Model With a Chaotic Prediction Model,* National Aeronautics and Space Administration, Goddard Space Flight Center, Greenbelt, Md., 554-FDD-911125, November 1991, each of which are incorporated herein by reference in their entirety.

Nonlinear dynamics allows the prediction of time series data more accurately than is possible using stochastic methods for time scales shorter than a characteristic horizon, and with about the same accuracy as using stochastic techniques when the forecasted data exceed this horizon. In some embodiments the horizon may be an Ashrafi Horizon as described in S. Ashrafi and L. Roszman, "Lyapunov Exponent of Solar Flux Time Series," *Proceedings of First*

Figure 3:
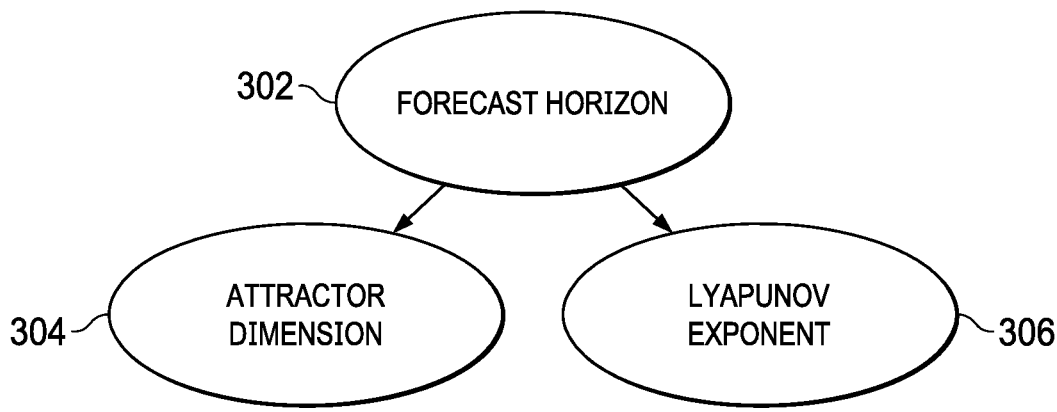
FIG. 3 illustrates a forecast horizon comprising a function of attractor dimensions and Lyapunov exponents.

*Experimental Chaos Conference*, June 1991 and S. Ashrafi and L. Roszman, Solar Flux Forecasting Using Mutual Information with Optimal Delay, AAS 93-311, Spaceflight Dynamics 1993, American Astronautical Society Publication, Advances in the Astronautical Sciences, Volume 84 Part II pages 901-913, each of which are incorporated herein by reference. As shown in FIG. 3, the forecast horizon 302 is a function of two dynamical invariants: the attractor dimension 304 and the Lyapunov exponent 306 as shown in S. Ashrafi and L. Roszman "Nonlinear Techniques for Forecasting Solar Activity Directly From its Time Series," *Proceedings of Flight Mechanics/Estimation Theory Symposium*. National Aeronautics and Space Administration, Goddard Space Flight Center, Greenbelt, Md. May 21-23, 1992 which is incorporated herein by reference. The techniques introduced herein are applicable to any time series of data generated from any physical, social or economic system.

Estimation of the attractor dimension 304 reconstructed from a time series of data has become an important tool in data analysis. Many possible characterizations of dimension have been introduced. Grassberger and Procaccia have introduced the notion of correlation dimension, which has become a popular method for estimating the attractor dimension for low-dimensional systems. In calculating the invariants of the system, the first necessary step is the reconstruction of the attractor for the system from the time-delayed values of the time series as shown in F. Takens, "Detecting Strange Attractors in Turbulence," *In Lecture Notes in Mathematics*, Vol. 898, 366 Berlin: Springer-Verlag, 1981, which is incorporated herein by reference. The choice of the time delay is critical for this reconstruction.

For an infinite amount of noise-free data, the time delay can, in principle, be chosen almost arbitrarily. However, the quality of the phase portraits produced using the time-delay technique is determined by the value chosen for the delay time. Studies by Fraser and Swinney such as those described in A. M. Fraser and H. L. Swinney, *Phys. Rev. A*33, 1134, 1986, which is incorporated herein by reference, have shown that a good choice for this time delay is the one suggested by Shaw, in R. S. Shaw, The Dripping Faucet as a Model Chaotic System, Aerial Press, C A, 1985, which is incorporated herein by reference, which uses the first local minimum of the mutual information rather than the autocorrelation function to determine the time delay. A refinement of this criterion is described hereinbelow and applies the refined technique to a sample time series data (solar flux data) to produce a forecast of the solar activity. However, the technique may be applied to any time series data.

Referring now to FIG. 4 there is illustrated a process for enabling an artificial intelligence system to forecast future values of data based upon a past time series group of data. The time series data is received at 402 and using this various dynamical invariants may be extracted at step 404. Using the dynamical invariants phase-space representations of the time series data are constructed at step 406. Phase-space representations comprise a space representation in which all possible states of a system are represented, with each possible state corresponding to one unique point in the phase-space. The phase-space representations are used for forecasting future values of the data at step 408. Numerical techniques enable construction of the phase-space representations of the time series data so that the future values of the time series data can be forecasted directly from its past time series. This approach makes it possible to model the behavior of a system using an attractor created in terms of extracted dynamical invariants from the system's dynamics without reference to any underlying physics or dynamics of the data. The dynamical evolution of time series in this reconstructed phase-space that captures the properties of the attractor, give a procedure for extracting an optimal time delay using mutual information, and present preliminary predictions made for the magnitude and phase of a sample data (next maximum).

Nonlinear Structure in Systems

Until recently, there was little reason to doubt that weather in principle is predictable, given enough data. Recently, a striking discovery changed this view. Simple deterministic systems with only a few degrees of freedom can generate seemingly random behavior. When a system exhibits apparent random behavior that is fundamental to its dynamics such that no amount of information gathering will make the system predictable, the system is considered chaotic. For example, much evidence supports the assertion that solar flux falls in this category. Perhaps paradoxically, chaos is generated by fixed rules that do not themselves involve any element of chance. The future of a dynamic system is completely determined by present and past conditions. In practice, amplification of small initial uncertainties makes a system with short-term predictability unpredictable in the long term.

New developments in chaos and nonlinear dynamics allow the modeling of the behavior of a system in terms of some invariants directly extractable from the system's dynamics, without reference to any underlying physics. Using chaos theory, short-term activity can be predicted more accurately than with statistical methods. In addition, chaos theory imposes a fundamental limit on accurate long-term predictions.

Review of Chaotic Dynamics

Self-Organization and Attractors

To gain an understanding of some of the concepts underlying nonlinear dynamics, consider a simple pendulum. The pendulum exhibits two fundamental degrees of freedom: position and momentum. However, in its stable periodic state (referred to as a limit cycle), the pendulum exhibits only one degree of freedom, the phase angle. The dynamics of the system are attracted to a lower dimensional phase-space, and the dimension of this reduced phase-space is equal to the number of active degrees of freedom in the system. The trajectory of the pendulum in phase-space is called the attractor for the system. Attractors are not limited to zero dimension (fixed points in phase-space) or one dimension (limit cycles, like the simple pendulum). For nonlinear systems, attractors can have higher dimensions and, in some cases, even fractional dimensions. When the attractor for a system has a fractional dimension, the attractor is a fractal and is referred to as a strange attractor. For non-linear systems, a generated attractor has a dimension equal to the number of active degrees of freedom in the system and these attractors can have multiple dimensions and in some cases fractional dimensions.

Phase-Space Construction Directly From a Time Series

When confronted with a complicated physical system, an experimenter normally measures at regular and discrete intervals of time the value of some state variable (for example, records the time series $s(t_0)$, $s(t_1)$, $s(t_2)$, . . . , with $s(t_i) \in \mathbb{R}$ and $t_i = t_0 + i\Delta t$. This comprises the creation of a time series sequence of data as mention above. From the observed time series, the experimenter attempts to infer something about the dynamics (for example, the physics) of the system. Because the time series is one-dimensional, it is an incomplete description of the system during its time evolution. Nevertheless, many features of the dynamics of the system can be inferred from the time series. Takens (F. Takens, "Detecting Strange Attractors in Turbulence," In *Lecture Notes in Mathematics*, Vol. 898, 366 Berlin: Springer-Verlag, 1981 which is incorporated herein by reference) and Packard et al. (N. Packard et al., "Geometry From a Time Series," *Phys. Rev. Lett.*, 45, 1980 which is incorporated herein by reference) have shown that for chaotic systems, the time series can be embedded into a higher dimensional space using time-delayed values of the series and thus recover the dynamics of the system. Vectors with components as:

$$X(t)=[s(t),s(t+s(t+\tau),s(t+2\tau),\ldots,s(t+(m-1)\tau)]^T$$

where $\tau$ (time delay) and m (the embedding dimension) are parameters of the embedding procedure. Here X(t) represents a more complete description of dynamics than s(t).

An embedding dimension of m>2D+1, where D is the fractal dimension of the attractor, almost always ensures the construction of the topology of the attractor (Takens' theorem). If unlimited, infinitely precise data are available, almost any delay time $\tau$ and embedding dimension m>D will work, at least in principle. However, choosing the optimal parameters for real data is a nontrivial process.

If T is too large, then the components s(t) and s(t+(m−1)τ) of the reconstructed vector will be effectively uncorrelated, which will cause inaccurate reconstruction of the attractor and thus inflate the estimated dimension of the system. On the other hand, if (m−1)τ is too small, then the components s(t), . . . , s(t+(m−1)τ) will all be very nearly equal, and the reconstructed attractor will fall near a long diagonal line. Thus, if the time delay is too large then it will cause an inaccurate reconstructions of the attractor and inflate the estimated dimension of the system, but if the time delay is too small then the reconstructed attractor will fall near a diagonal line. Generally, T (time delay) must not be less than some characteristic decorrelation time, and (m−1)τ must not be too much greater than this decorrelation time. One such characteristic of time is the local minima of the autocorrelation function. This criterion gives only the linear dependence of the function s(t) with s(t+τ) The system here is nonlinear. Therefore, the mutual information of the system is a better property to use to select the optimal delay because the mutual information is (roughly) a nonlinear analogue of the autocorrelation function. That is, the mutual information is a property that shows the general dependence of s(t+τ) on s(t) rather than its linear dependence.

As an example, after embedding the time series in a state space using the Ruelle-Takens-Packard delay coordinate technique, the induced nonlinear mapping is learned using a local approximation. This procedure enables short-term forecasting of the future behavior of the time series using information based only on past values. Farmer and Sidorowich (J. Fanner and J. Sidorowich, "Predicting Chaotic Time Series," *Phys. Rev. Letts.*, 59, 1987 which is incorporated herein by reference) have already developed the error estimate of such a technique:

$$E \approx Ce^{(m+1)KT}N^{(m+1)/D}$$

where E=normalized error of prediction (0≤E≥1, where 0 is perfect prediction and 1 is a prediction no better than average)
m=order of local approximation
K=Kolmogorov entropy
T=forecasting window
N=number of data points
D=dimension of the attractor
C=normalization constant Using the Fanner-Sidorowich relation, the prediction horizon T for the zeroth order of local approximation can be found at step 206. Any prediction above Tmax is no better than an average constant prediction, where $T_{max}$ is found using:

$$E(T_{max})=1$$

For m=0, K is the largest Lyapunov exponent λ. Therefore, $T_{max}$ can be calculated from:

$$e^{KT_{max}}N^{-1/D} \approx 1$$

which can be written as:

$$T_{max} \approx \frac{\ln(N)}{KD} \approx \frac{ln(N)}{\lambda D}$$

Any prediction beyond the indicated horizon (Ashrafi-Conway Horizon) is no better than an average value. The connection between the local and the global Lyapunov exponents has recently been found by Abarbanel et al. (H. Abarbanel et al., "Lyapunov Exponents in Chaotic Systems," *Rev. Modern Phys. Letts.* (BJ, (in press) which is incorporated herein by reference) to be a power law of the form:

$$\lambda(1)=\lambda_G+c/l^v$$

where λ(1)=local Lyapunov exponent
l=length of observed data (observation window)
v=a constant dependent to the dynamical system (0.5≤v≤1.0)
c=a constant dependent to initial conditions of the system
$\lambda_G$=well-known global Lyapunov exponent
ω=frequency of data points Because any data set has a finite length, the Abarbanel-Kennel power law and Farmer-Sidorowich relation can be used to show that Tmax must have the form:

$$T_{max} \approx \frac{\ln(l\omega)}{(\lambda_g + c/l^v)D}$$

This equation shows that as l increases linearly, Tmax increases logarithmically (point of diminishing return).

Structure of the Forecasting Algorithm

Once the state space representation is known, the next goal is to fit a model to the data to generate predictions at step 210. Several methods can be used. The simplest method is to assume that the dynamics can be written as a map in the form:

$$X_{n+1}=M(X_n)$$

where the current state is Xn, and Xn+1 is a future state. Methods such as the polynomial method, rational approximation, radial basis functions, neural networks, and local approximations have all proven to be successful approaches to modeling. The local approximation technique is described here because it is the method used to structure the forecasting algorithm presented in this patent. A description of some of these modeling techniques is described below.

Local Approximation

The basic idea of this approach is to break up the domain of M into local neighborhoods and fit different parameters into each neighborhood. This fit is generally better than global approximation, especially for large data sets. Most global representations reach a point of diminishing return. At this point, adding more parameters or data gives only an incremental improvement in accuracy. After a certain point, adding more local neighborhoods is usually more efficient than adding more parameters and going to a higher order. With local approximation, it is possible to use a given functional representation efficiently. The key is to choose the local neighborhood size correctly, so that each neighborhood has just enough points to make the local parameter fit stable. Thus, adding more parameters or given data gives only an incremental improvement in accuracy so it is important to choose the local neighborhood size correctly when doing local approximation.

An example of local approximation is the first order, or nearest neighbor, approximation. This approach involves looking through the data set for the nearest neighbor to the current point and predicting the evolution of the state based on what the neighbor did at later times. This may also be described as establishing a sphere around a present point, where the sphere encompasses the nearest neighborhood points and the present point comprises the current point. Thus as illustrated in FIG. 5, to predict future occurrences such as tomorrow's solar flux or another recurring data pattern using local approximation to first order, it is necessary to search the historical record at step 502 and find the solar flux or other data pattern most similar to that of today at step 504. Tomorrow's solar flux or other data pattern should be the same as the neighboring pattern one day later may be determined at 506. This determined future pattern may be used to determine future data values at step 508 using an AI system. Referring now also to FIG. 6, first order approximation can sometimes be improved by finding more neighbors at step 602, generating predictions for each of the additional neighbors (spheres) at step 604 and merging their predictions at step 606, for example, by weighting according to distance from the current state. When the data is noisy, it is better to use a larger number of neighbors (spheres). This procedure can be improved by weighting the contributions of neighbors (spheres) according to their distance from the current state. The advantage of linear approximation is that the neighborhood size grows slowly with the embedding dimension. The order of approximation may depend on factors such as the choice of neighborhoods, the dimension, or peculiarities of the data set. For low-dimensional problems, a third order approximation is good enough.

Finding neighbors (spheres) in a multidimensional data set is time consuming when considering many points. A straightforward method is to compute the distance to each point when finding neighbors in a multidimensional data set, which takes approximately N steps for N points. This method can be reduced to roughly log N steps by organizing the data with a decision tree, such as a k–d tree. This approach has been taken for the models presented here.

To implement this approach, the parameters required for the reconstruction of the attractor (step 208) must be determined accurately. This determination will be discussed in the remainder of this section.

Choice of the Embedding Dimension d

In this section, the technique used to determine the correct value of the embedding dimension d from the scalar time series x(n), n=1, 2, . . . , $N_D$ will be covered. There must be enough data in the time series to remove concerns with statistical issues about numerical accuracy. Extrinsic noise in the data will be ignored for this analysis. By following Takens' phase-space attractor reconstruction technique for the time series, the dynamics of the system will be captured and embedded in phase-space. This procedure requires a correct choice of τ (time shift), which will be discussed in the next section.

Figure 7:
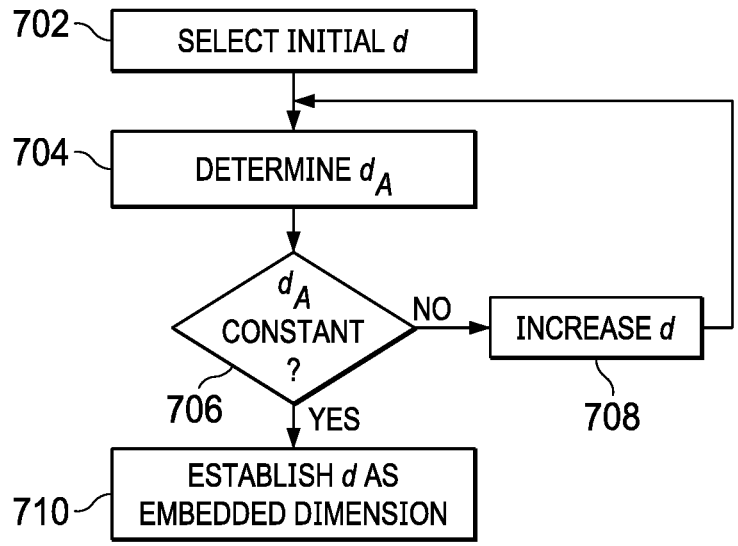
FIG. 7 illustrates a flow diagram of a process for establishing and embedding dimension.

Referring now to FIG. 7, there is illustrated a flow diagram of the process to establish an embedding dimension. To establish the embedding dimension d, a characteristic of the attractor that becomes unchanging as d becomes large is needed. This invariant characteristic of the attractor is the attractor dimension $d_A$. An initial value of d is selected at step 702 and an attractor dimension $d_A$ is determined at step 704. Inquiry step 706 determines if the attractor dimension is constant. If not, one increases d at step 708 until inquiry step 706 determines $d_A$ becomes constant and identifies the minimum d where $d_A$ "saturates" as the embedding dimension at step 710. Computation of $d_A$ is difficult, so the correlation function D(r) proposed by Grassberger and Procaccia in P. Grassberger and I. Procaccia, *Phys. Rev. Lett.* 50, 346, 1983, which is incorporated herein by reference is used for computing $d_A$. The correlation function is given by:

$$D(r, N, d) = \frac{2}{N(N-1)} \sum \sum U(r - \|X(j) - X(i)\|), i \neq j$$

where U(r) is the unit step function. For large values of N, the behavior of D (r, N, d) for r becomes independent of N and takes the form:

$$D(r,N,d)=\Phi(r,d)r^{v(d)}$$

By plotting D(r, N, d) versus r, the correct value of the dimension d can be singled out.

Choice of the Time Shift τ

The optimal choice of τ has been discussed extensively in the literature such as J. H. Bentley, "Multidimensional Binary Search Trees in Data Base Applications," *IEEE Transactions on Software Engineering*, 5 (4), 1979, which is incorporated herein by reference. Previous studies of the solar activity set i equal to the first local minimum of the autocorrelation function. The work of Fraser and Swinney suggests that a better criterion for the choice of the time delay is given by the first local minimum of the mutual information for the system. In this work, a modification of that criterion is used to forecast the sample time series.

Mutual Information

The autocorrelation function is given by:

$$R(\tau)=\int_{-\infty}^{\infty} f(t)f(t+\tau)dt$$

This function measures the linear dependence of the function ƒ(t) with the time-shifted function ƒ(t+τ). Because the system under study here is nonlinear, the mutual information of the system is a better choice of functions if the optimal time delay is to be determined. The mutual information is a measure of the general dependence of the function with its time-shifted value, rather than a measure of the linear dependence. The mutual information between a time series Q and the time-shifted series S is given by:

$$I(S,Q)=I(Q,S)=H(Q)+H(S)-H(S,Q)$$

where H(Q) is the entropy of system Q, given by:

$$H(Q)=-E_i P_q(q_i)\log P_q(q_i)$$

and H(S, Q) is the joint entropy of systems S and Q, given by:

$$H(S,Q)=E_{ij}P_{sq}(S_i,q_j)\log P_{sq}(S_i,q_j)$$

Pq and Psq in these equations are the probability densities for the corresponding states. The mutual information calculated in this manner gives a general measure of the independence of the time series S (the original time series shifted by the amount τ) relative to the time series Q.

Computation of Mutual Information.

Figure 8:
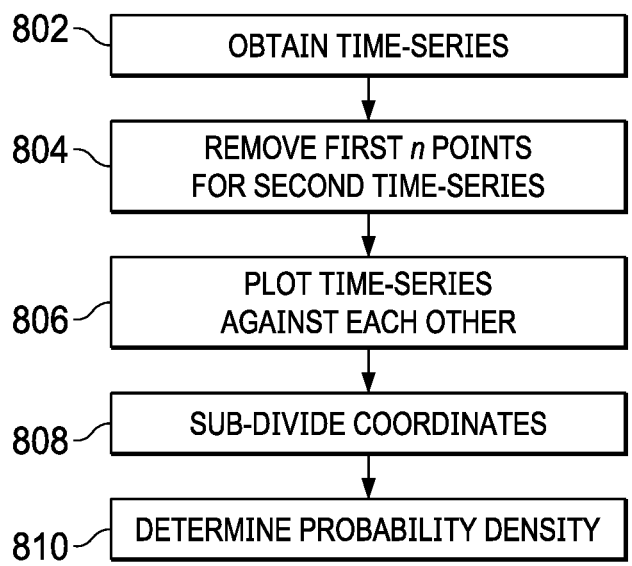
FIG. 8 illustrates a flow diagram for computing mutual information.

Because the mutual information is basically a sum of entropies, the probability density P for S, Q, and the joint system must be calculated. For a time series, this calculation cannot be performed analytically. An approximation to the calculation is possible following the prescription given in Fraser and Swinney. The procedure can be summarized as follows as shown in FIG. 8. Let Q be the original time series at step 802, and let $S_n$ be the series with the first n points removed at step 804. Plotting Q against $S_n$ at step 806 produces a curve in a two-dimensional space that is used in the calculation of I(S, Q). Because the time series has a finite number of elements, a finite number of points occurs in the space of the system. Now subdivide each coordinate in the space at step 808 so that the same number of points falls in each of the subdivided regions. Thus, if the time series has i elements, the Q-axis is divided at location $q_j$, chosen so that there are i/2 elements with q component greater than $q_j$, and i/2 elements with q component less than $q_j$. The $S_n$-axis is divided in a similar manner. When the system is divided in this manner, the probabilities P(Q) and $P(S_n)$ for the components q and $S_n$ of any point are the same for each region. This process simplifies the calculation of the mutual information because the only nontrivial probability density in the equation for $I(S_n, Q)$ is the mutual probability density, Psq.

Once the division of the coordinate axes has been accomplished as described above, the space of the two-dimensional system is divided into four regions. The probability that a randomly selected point in the system (but not in the original time series) will fall in region m of the space can be approximated at step 810 by:

$$P_m = \frac{n_m}{N}$$

where $n_m$ is the number of points from the time series that lie in region m, and N is the total number of points in the time series. This procedure can be repeated, dividing the regions into subregions, dividing the resulting subregions into sub-subregions, and so on, until the approximate probability density calculated using this technique becomes an accurate representation of the true probability density of the system.

Two cautions are in order here. First, the depth of the subdivisions must not be too shallow. If it is, then the resulting probability density will not accurately reflect the details of the true density. Second, if the subdivisions are made too often, the resulting probability density will pick up fluctuations arising from the discrete nature of the time series and will be bumpier than the true probability density. Thus, the criteria for halting subdivision of the regions must be handled carefully. The procedure taken here is to halt subdivision if the resulting subregions are equiprobable to within a specified tolerance. This tolerance is taken to be 20 percent as measured using a x-square test in this patent.

A Simple Model System

To test the effectiveness of the mutual information algorithm, several model systems have been analyzed. To illustrate the results, the Rossler system will be examined. The equations that describe a Rossler system are:

$$\frac{dx}{dt} = -y - z$$

$$\frac{dy}{dt} = x + 0.2y$$

$$\frac{dz}{dt} = 0.2 + xz - 5.7z$$

Figure 9:
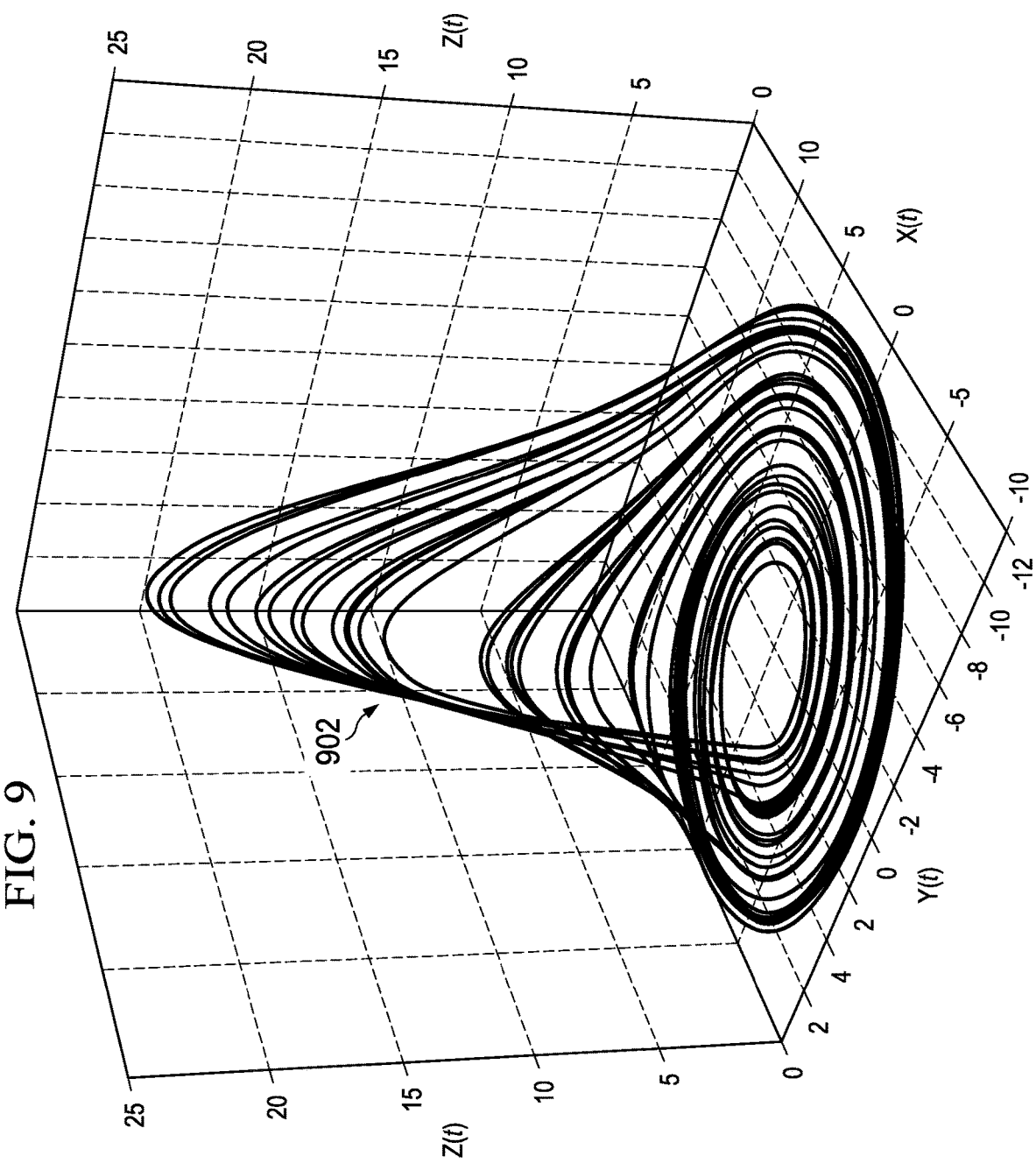
FIG. 9 illustrates a Rossler attractor.
Figure 10:
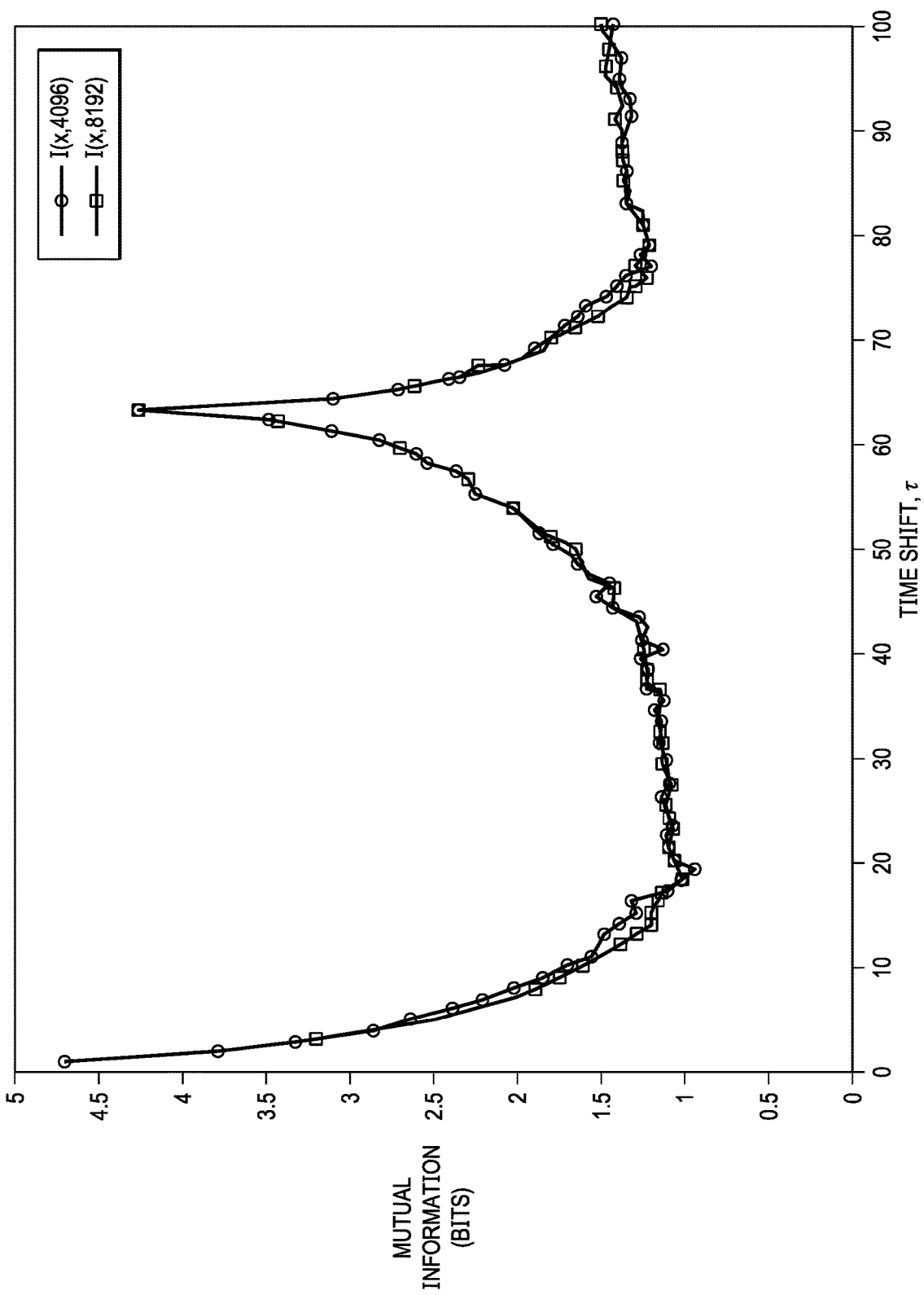
FIG. 10 illustrates mutual information for Rossler 4096 and 8192 points.

These equations have been integrated numerically using a fourth order Runge-Kutta algorithm with a fixed step size of $\Delta t = 0.05$. The system produces the chaotic attractor 902 shown in FIG. 9 that is a Rossler Attractor. A Rossler system is a system of three non-linear ordinary differential equations originally studied by Otto Rossler. These differential equations define a continuous-time dynamical system that exhibits chaotic dynamics associated with the fractal properties of the attractor. An orbit within the attractor follows and out spirals close to the X, Y plane around an unstable fixed point. Once the graph spirals out enough, a second fixed point influences the graph, causing a rise in twist in the Z dimension. In the time domain, it becomes apparent that although each variable is oscillating within a fixed range of values, the oscillations are chaotic. This attractor has some similarities to the Lorenz attractor, but is simpler and has only one manifold. The data generated for the x, y, and z coordinates of the system have been treated as independent time series, and the resulting mutual information for these time series has been calculated using the algorithm described above. The mutual information for the x-coordinate as a function of the time shift is shown in FIG. 10. It illustrates mutual information for Rossler 4096 points 1002 and 8192 points 1004.

The Rossler system illustrates the features of good and bad choices of the time delay. The goal of the analysis of the mutual information is the selection of the time shift which given a time series, best reconstructs the attractor of the system using the Ruelle-Takens-Packard technique. The suggestion that the first local minimum of the mutual information produces the optimal time shift can be examined for this system. For convenience, consider the time series constructed from the x coordinate data for the system. As can be seen in FIG. 10, the first local minimum occurs at about t=32 steps–1.6 time units. (Note that minima that occur due to fluctuations arising from the discrete nature of the time series are omitted.) The time shift suggested is therefore τ=1.6. Because the Rossler system is three-dimensional, this choice gives the location of the points on the reconstructed attractor as:

$$\vec{r_i} = [x(t_i), x(t_i+1.6), x(t_i+3.2)]^T$$

Figure 11:
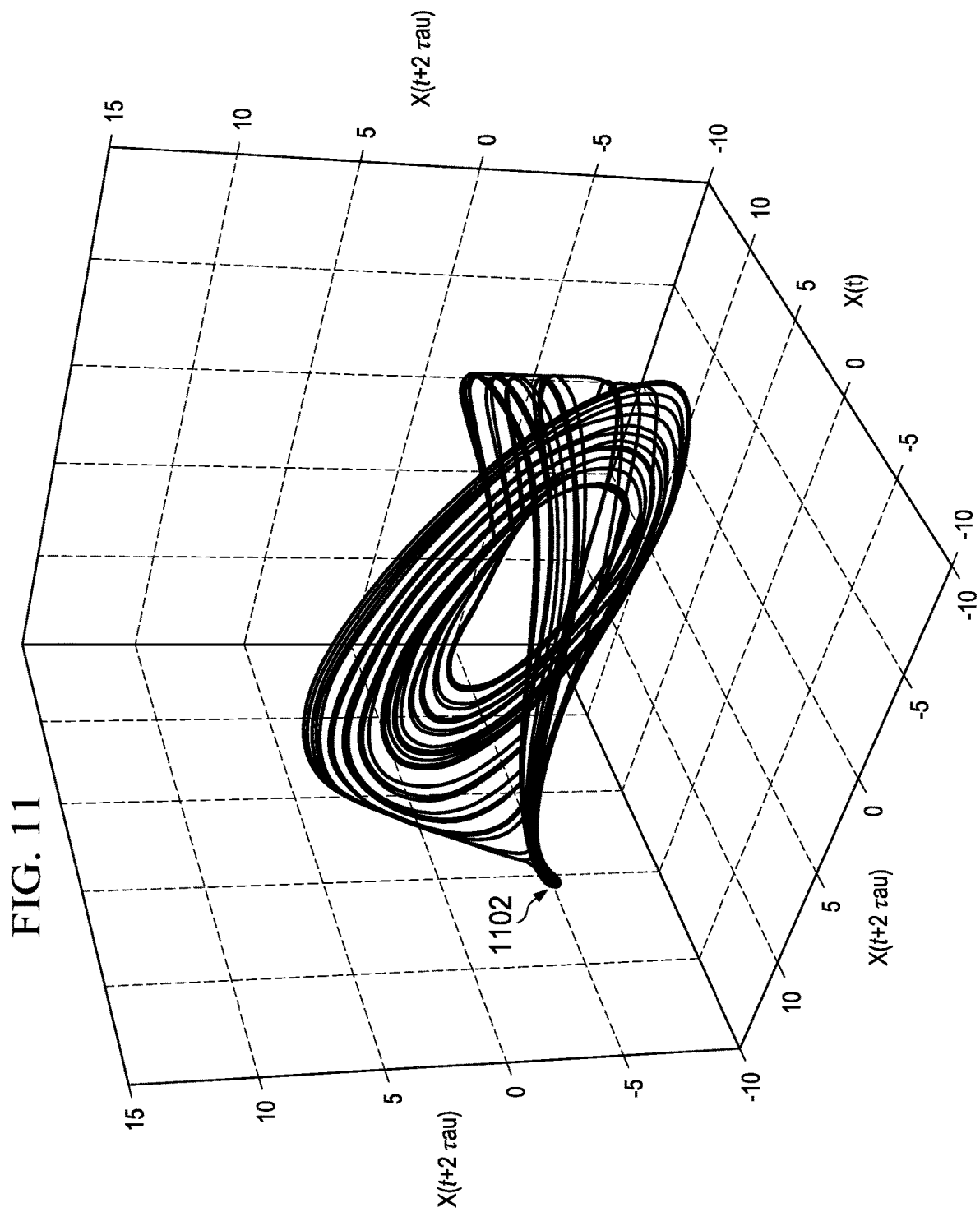
FIG. 11 illustrates a first embodiment of a reconstructed Rossler attractor.

When the resulting vectors are plotted in phase-space, the attractor does resemble the original system (see FIG. 11). Adjacent sections along the trajectory are spaced in the same way as on the original attractor. The time series does not contain information about the range of the y or z variables, so the actual orientation and scaling of the reconstructed attractor are different than for the actual system.

Figure 12:
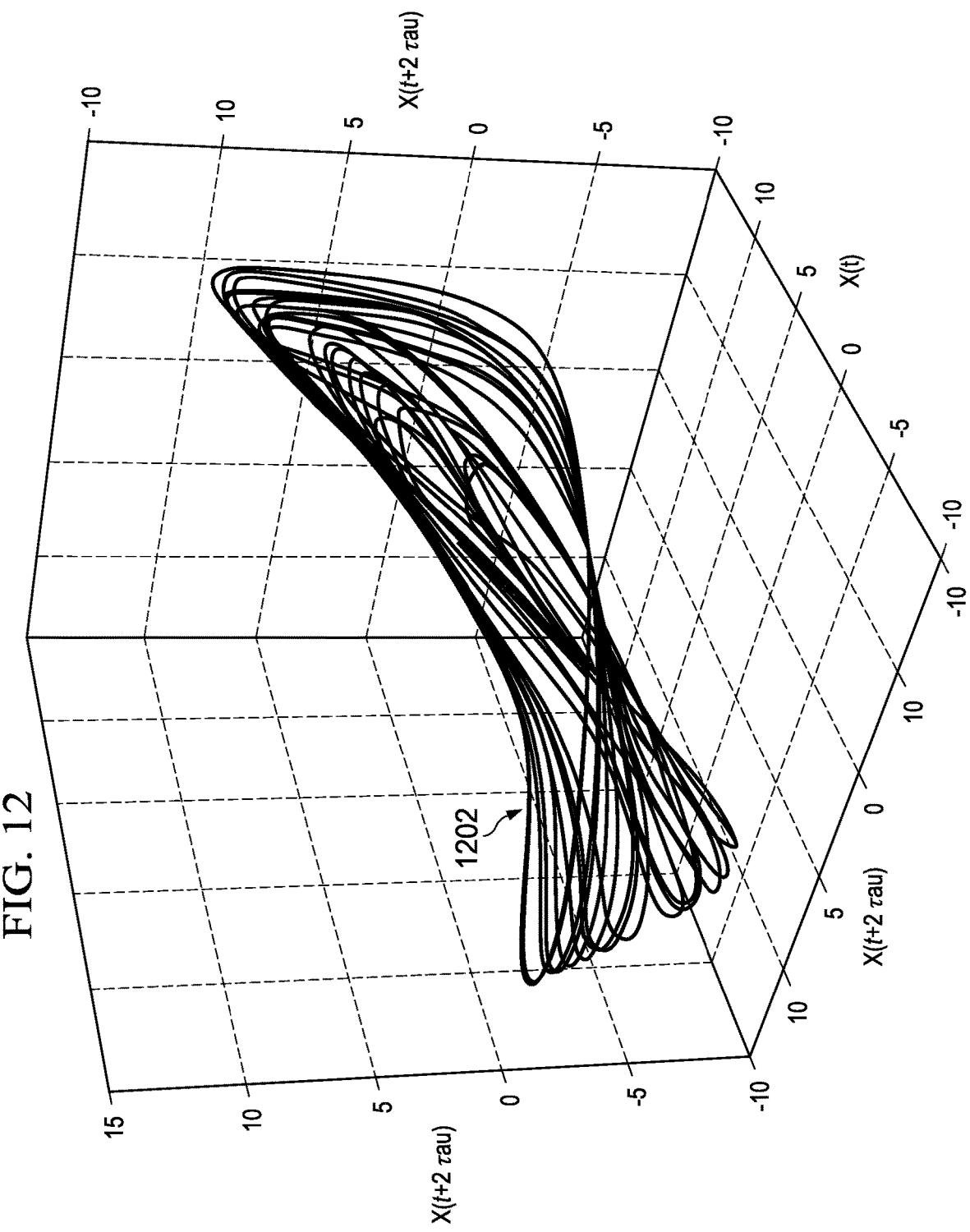
FIG. 12 illustrates a second embodiment of a reconstructed Rossler attractor.

For the purposes of prediction, the reconstructed attractor shown in FIG. 11 has one disturbing feature. For one specific region 1102 through which many trajectories pass (the cusp on the left side of the phase portrait), any prediction made across this region will be inaccurate. However, a better choice exists for the time delay than that made above. This better choice is seen by first examining a much worse choice. Suppose that the first local maximum of the mutual information is chosen for the time shift, so that i=3.15. The reconstructed attractor 1202 for this choice is shown in FIG. 12. This reconstructed attractor 1202 does not preserve even the appearance of the original attractor 902. This difference is explained by considering what the mutual information tells about the system. The mutual information is a measure of the dependence of the system with the time delayed version of itself. For reconstruction, the reconstructed axes should be as orthogonal to one another as possible. This pseudo-orthogonality produces the optimal spread in the trajectory of the attractor and, therefore, the best reconstruction for forecasting the system. The problem with the reconstruction 1202 based on τ=1.6 is that the (t+2τ)-axis hits near the first local maximum of the mutual information and is, therefore, far from satisfying the pseudo-orthogonality criterion. In this work, the axes are made pseudo-orthogonal by finding the time shift τ that minimizes the murual information at each of the time-shifted values of τ. That is, the optimal choice of the time shift for a d-dimension system is found by minimizing:

$$I_t = \sum_{j=1}^{d-1} I(\tau_j)$$

Figure 13:
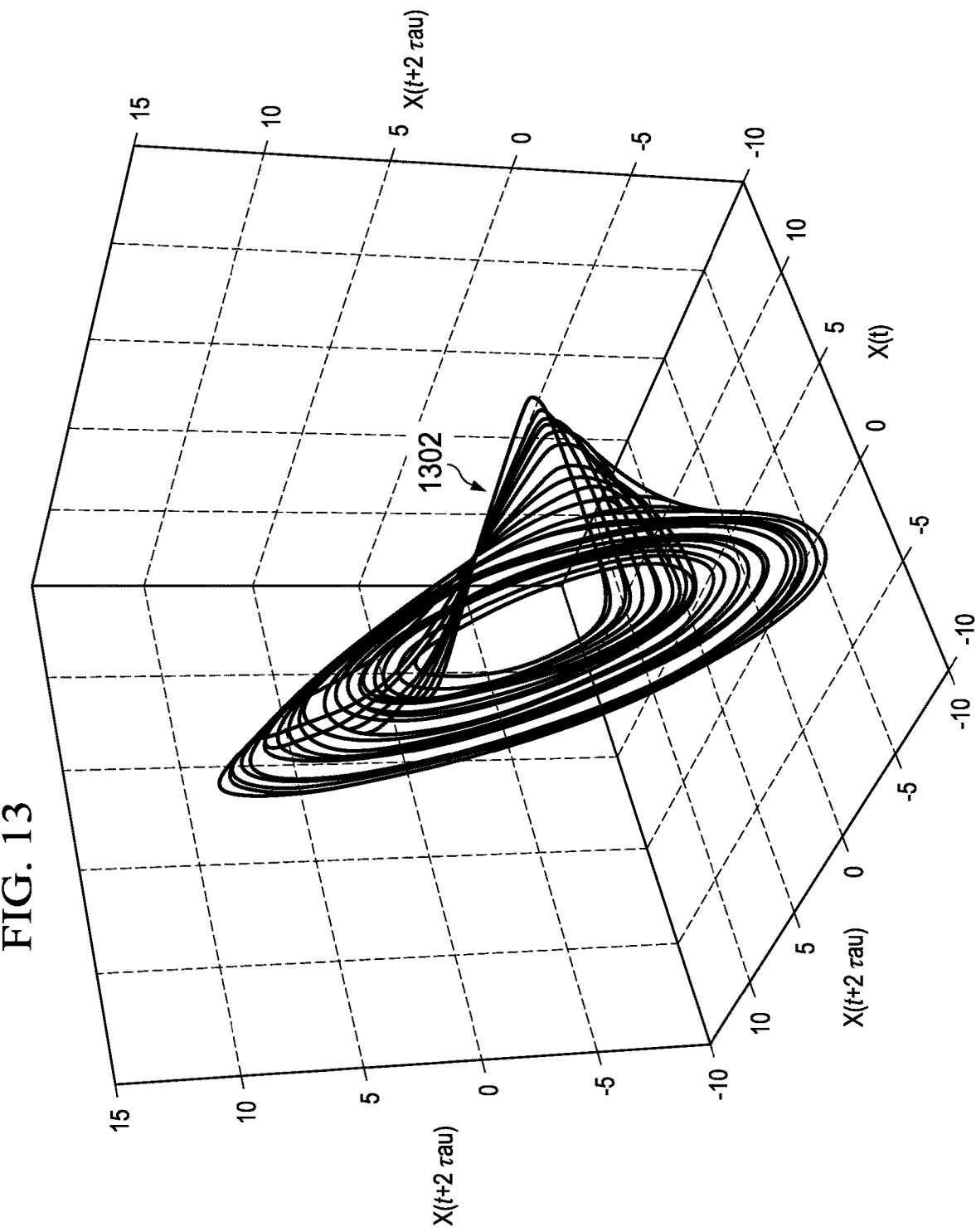
FIG. 13 illustrates a third embodiment of a reconstructed Rossler attractor.
Figure 14:
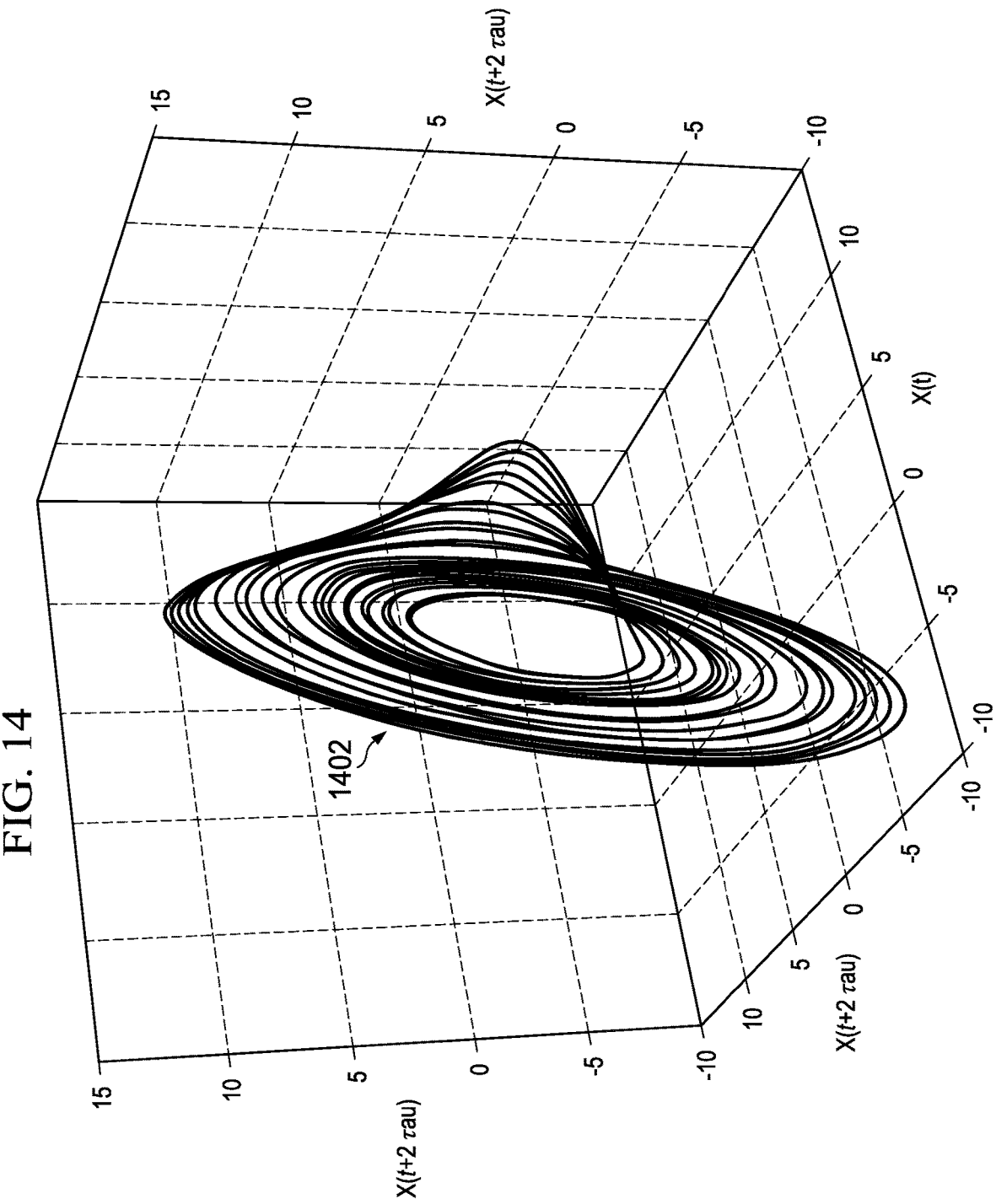
FIG. 14 illustrates a fourth embodiment of a reconstructed Rossler attractor.

For the Rossler system, this minimization indicates that a time delay of τ≈0.85 should be used when reconstructing the attractor. The resulting system is shown in FIG. 13. For comparison, the reconstruction 1402 using a time delay of τ=0.40 is shown in FIG. 14. The optimal reconstruction 1302 shows the best spread of the trajectories possible given the limitations of the time series data. Therefore, it is this optimization criterion that must be applied to the time series for the solar flux data to produce the best reconstructed attractor on which to forecast.

Preliminary Forecasts of the Solar Flux or Other Data

Figure 15:
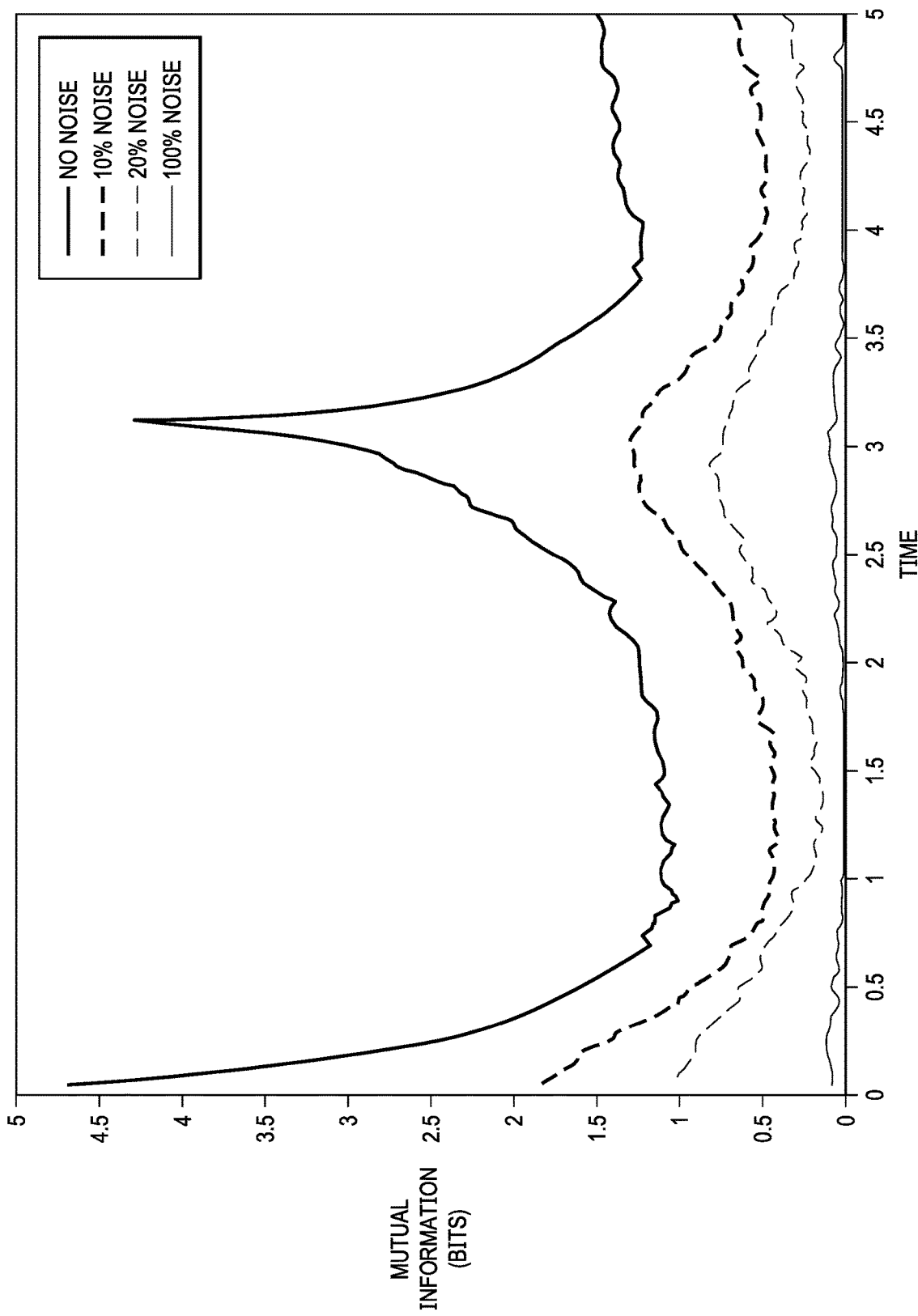
FIG. 15 illustrates mutual information of a Rossler attractor with noise.

Solar flux or other data is not noise free. The goal of this work is to determine the optimal time shift for the reconstruction of the attractor for the solar flux or other data. Because the criterion chosen for the determination of this time shift depends on the mutual information, the effects of noise on the mutual information should be examined. FIG. 15 shows the effect of additive noise on the mutual information for the Rossler system. The extremas of the mutual information remain fixed in position but are reduced in amplitude. The optimal time shift calculated from this mutual information function is identical to that calculated for the noise-free system.

The techniques described herein have been used to produce preliminary forecasts for the behavior of $F_{10.7}$, but they can be used for any time series data. To produce forecasts that extend reasonably far into the future, it was necessary to build a time series that represents $F_{10.7}$ measured approximately once a month. However, because the resulting time series should represent the actual features of the data, rather than reflect the artificial constraints imposed by the calendar, the procedure described below was used.

Figure 16:
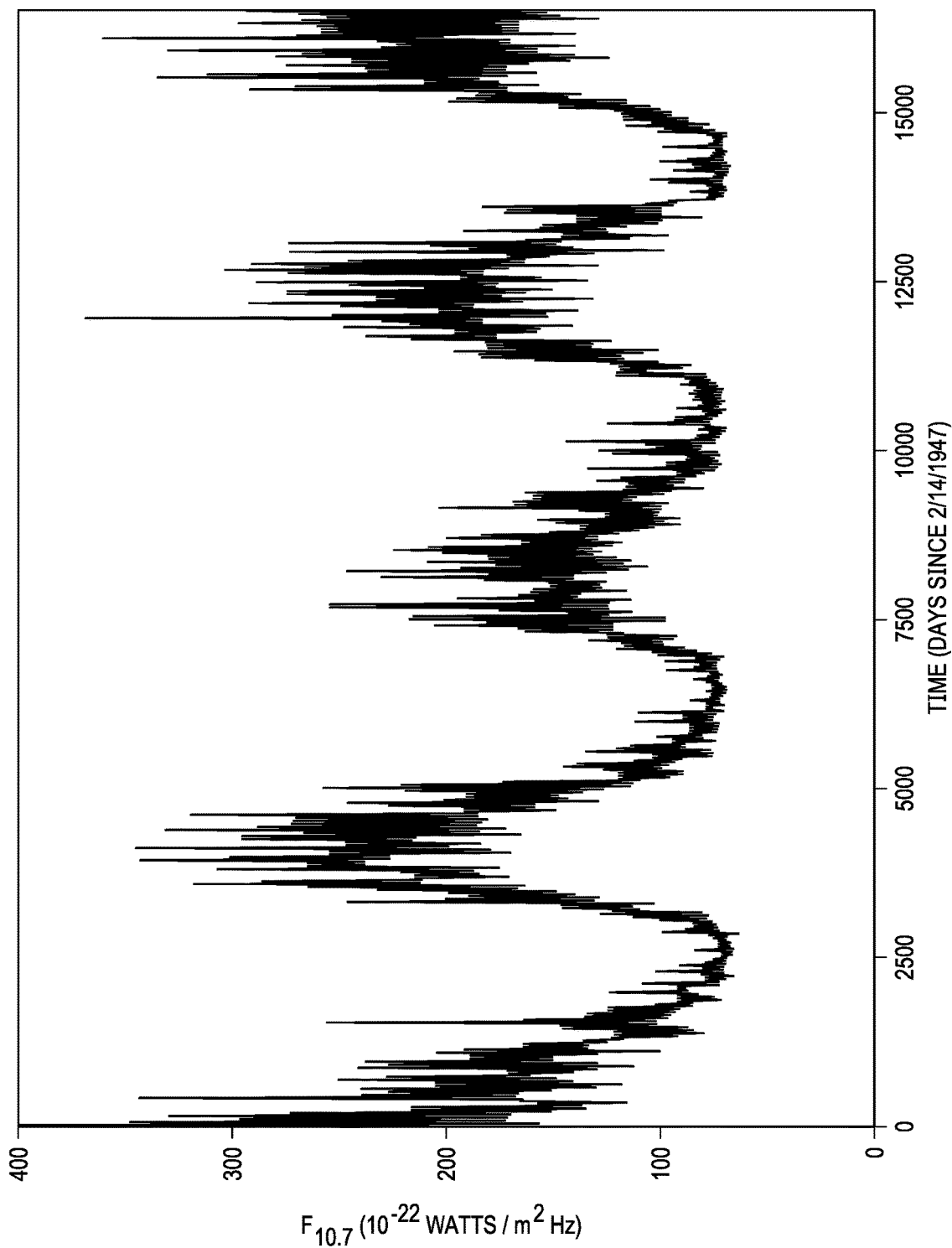
FIG. 16 illustrates a daily solar flux time series.
Figure 17:
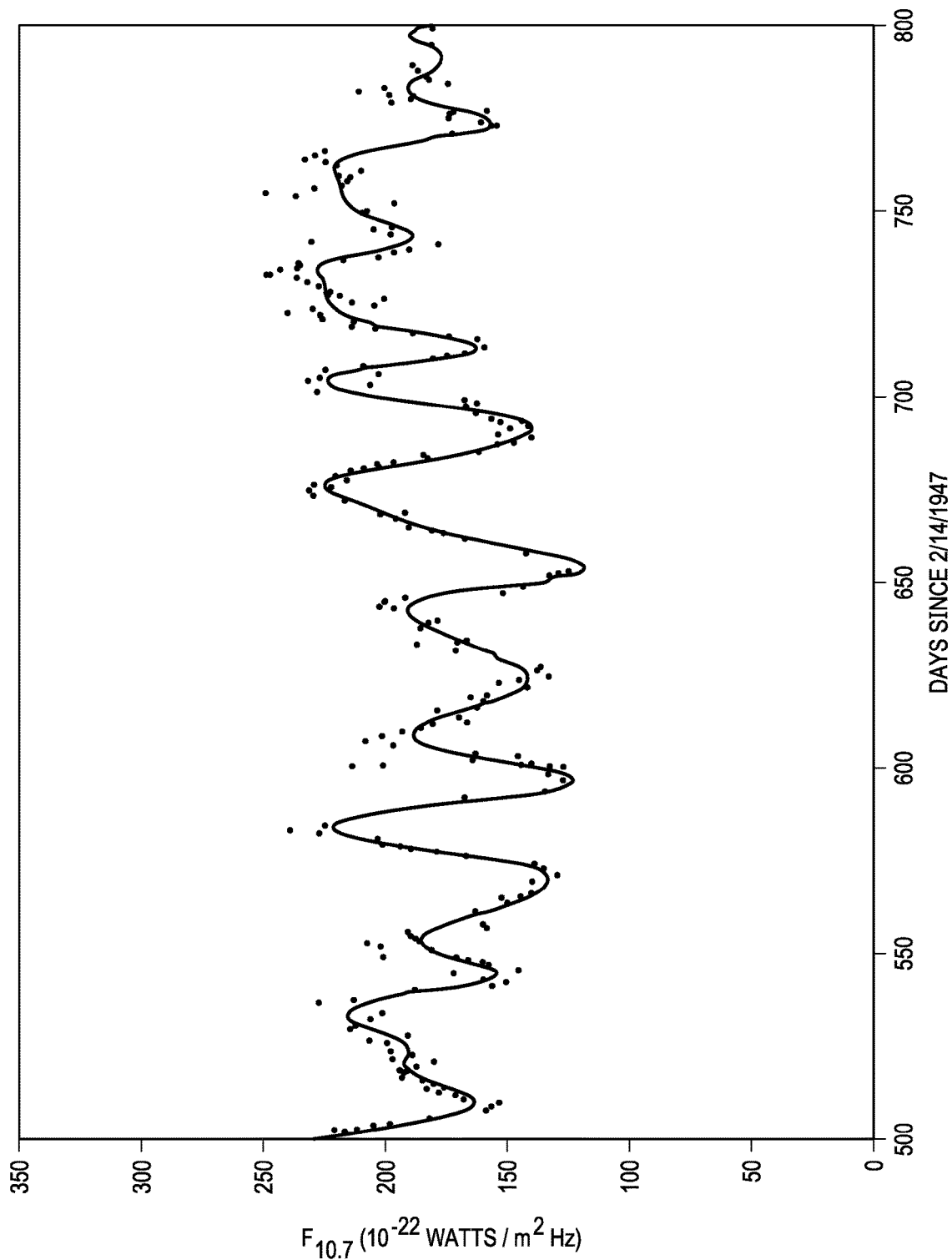
FIG. 17 illustrates filtered and unfiltered daily solar flux.
Figure 18:
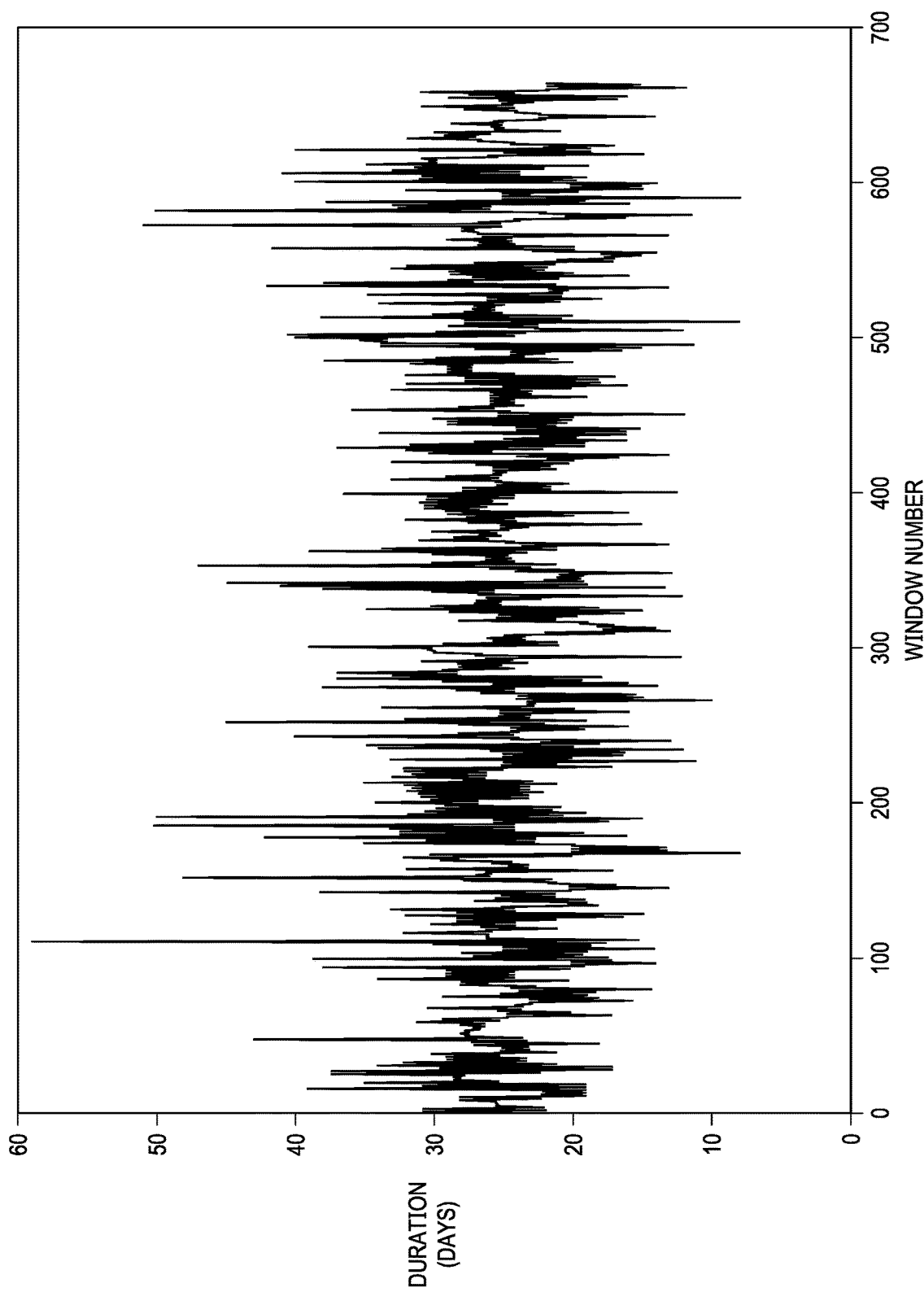
FIG. 18 illustrates variations of the period between minimas.
Figure 19:
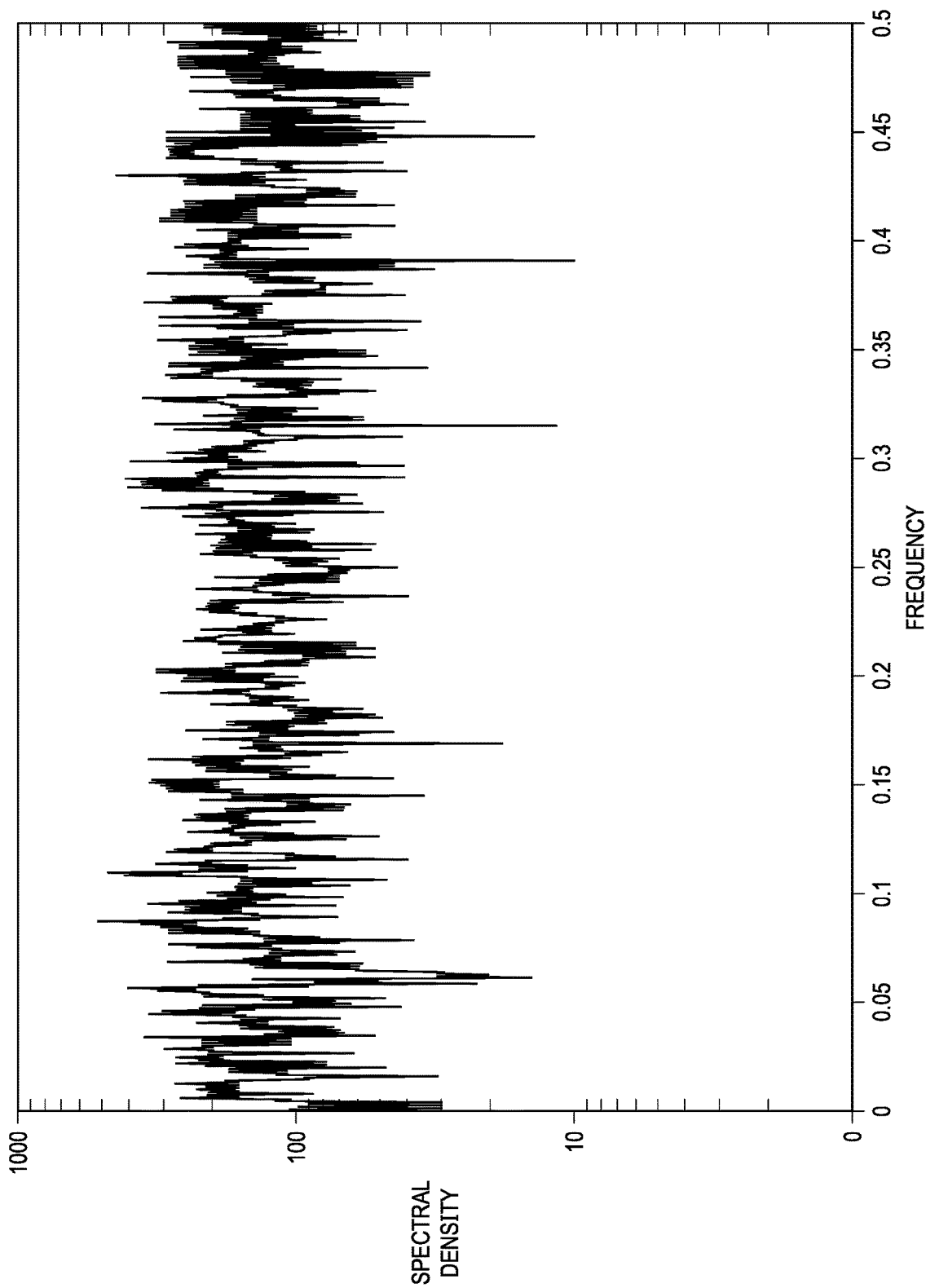
FIG. 19 illustrates the power spectrum of variations between minimas.
Figure 20:
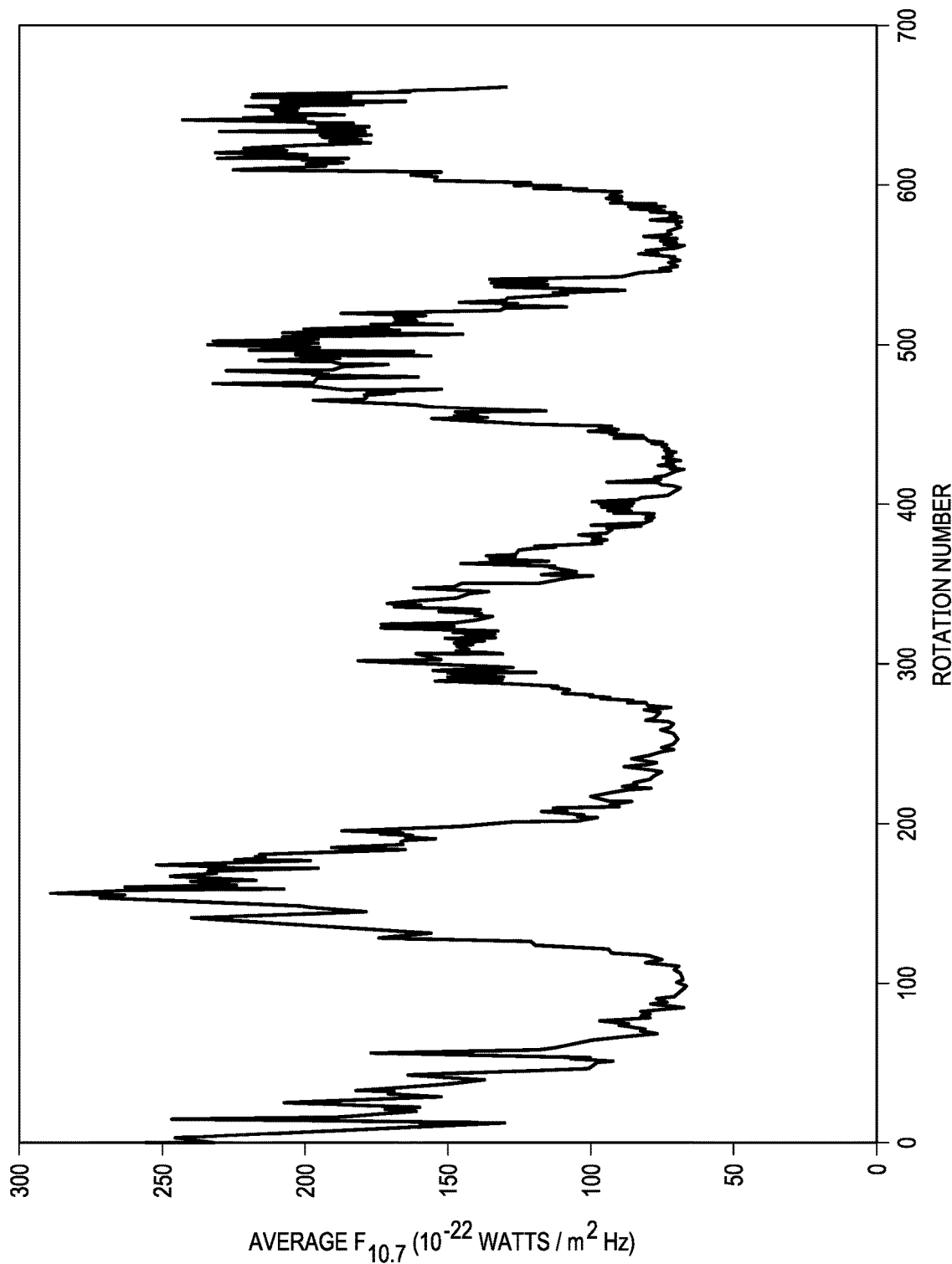
FIG. 20 illustrates solar flux averaged over solar rotations.

The daily solar flux is shown in FIG. 16. The data for the flux have been smoothed using Fourier techniques, and the results of this smoothing are shown in FIG. 17. One interesting feature of the resulting time series is the location of the extremas for the data. The minimas and maximas do not occur periodically. The phasing of the extremas is an important feature of the data, and it is the most difficult feature to forecast using nonlinear dynamics. This feature can be seen by examining the period between the minimas for the data. FIG. 18 shows the variation in the timing of the extremas. If these data are used to calculate the power spectrum of the phasing, then the amplitude is nearly uniform at all frequencies (FIG. 19). This case corresponds to a large Lyapunov exponent for the system, which means that the system is much more stochastic than can be handled using nonlinear techniques. Nevertheless, the amplitude of $F_{10.7}$ can be effectively forecast because the corresponding Lyapunov exponent is small and positive. The "monthly" time series is then constructed by taking the daily data and averaging it between the minimas of the series. The average period of the minimas is found to be about 24.8 days; this period is used to set the time scale for the data. The resulting time series is shown in FIG. 20. Thus, if the Lyapunov exponent is less than zero, the system is considered deterministic, if the Lyapunov exponent is greater than zero but less than one, the system is chaotic, and if the Lyapunov exponent is anything greater than one the system is stochastic.

Figure 21:
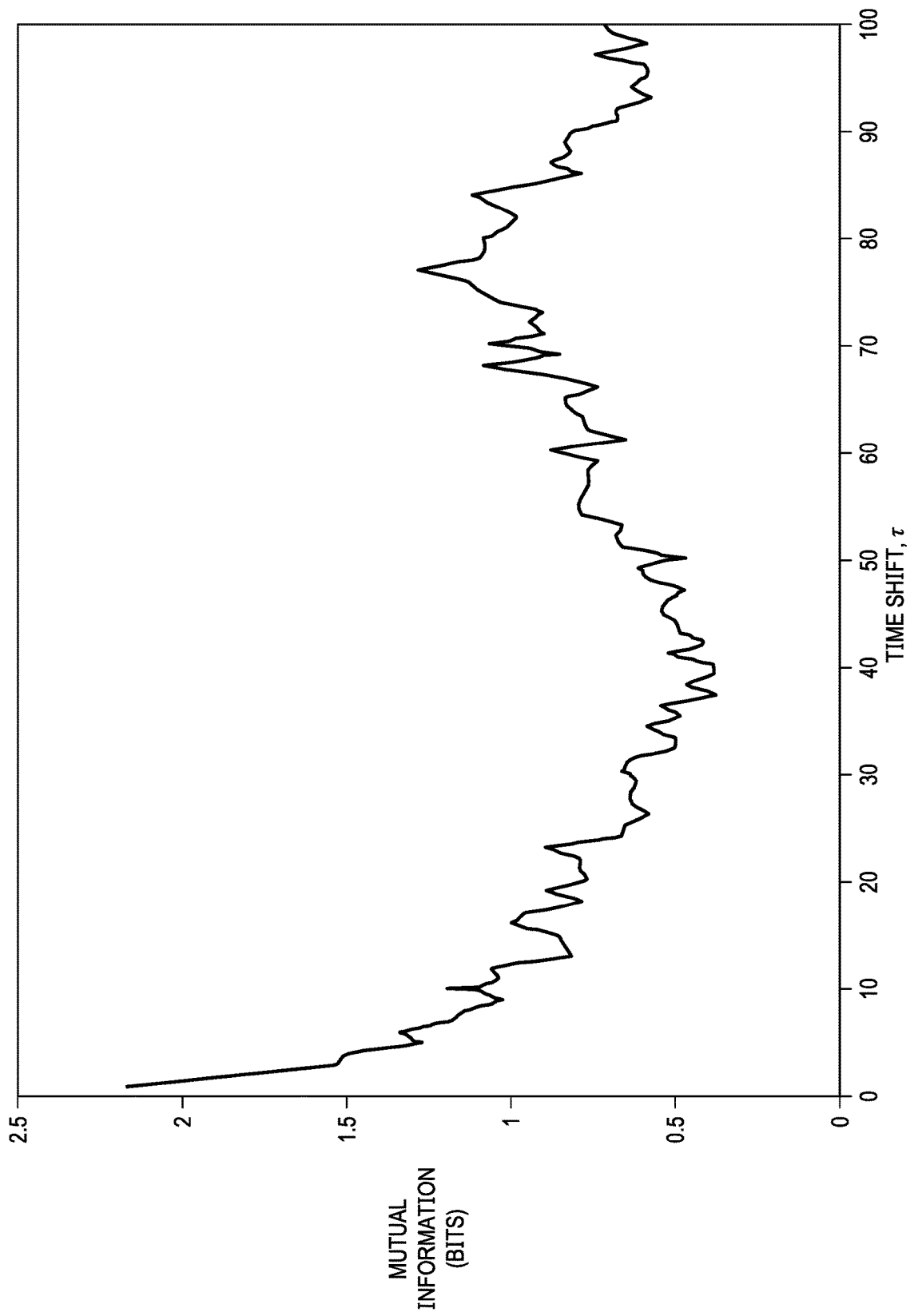
FIG. 21 illustrates mutual information of averaged flux.
Figure 22:
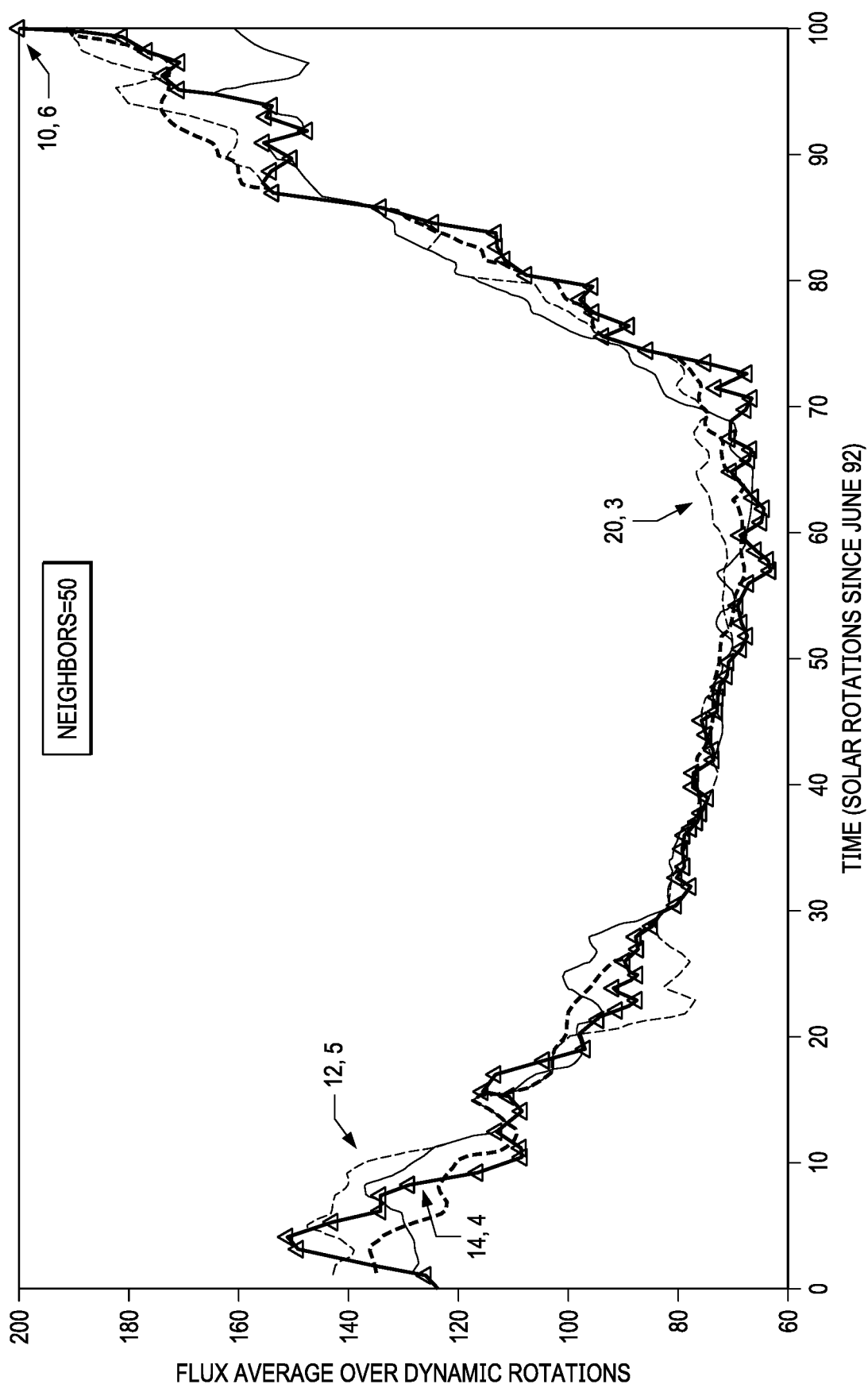
FIG. 22 illustrates a preliminary solar flux forecast.

The mutual information for the monthly time series is shown in FIG. 21. The function is not as smooth as those presented earlier because the time series is not as large as that used for the Rossler system, so that statistical fluctuations become more apparent. The optimal time shift can be calculated for this system given the embedding dimension of the attractor. The attractor can then be reconstructed, and forecasts of the behavior of $F_{10.7}$ can be made. These forecasts are shown in FIG. 22 for several different dimensions. The predictions made so far have several deficiencies. The time scale is in terms of periods of $F_{10.7}$ which has averaged about 24.8 days over the past 40 years. This period fluctuates from as little as 10 days to as much as 60 days (see FIG. 18) and, therefore, produces uncertainty in the time scale of the predictions. The dimension and Lyapunov exponent for $F_{10.7}$ have not yet been calculated. These data are needed to develop the time horizon for our predictions. All of these parameters must be computed in order to fine-tune the predictions made using these techniques.

The data set used for the forecasts covers four solar cycles. A larger data set is needed to enhance the large time scale forecasting capabilities of our method. These data should allow forecasts of the solar cycle using nonlinear dynamics.

Any time series that has an inherent pattern can be forecasted using the techniques described herein above. The above example illustrates using a complicated time series as a sample data (i.e. Solar Activity). Using the described techniques, the complicated physical models are bypassed and the future forecasted directly from past observation. In other words, the nuclear, thermodynamics, electromagnetic flux of sun spots, mechanical rotation, fluid dynamic models of the sun are bypassed and reconstructed a new model reconstructed that bypasses all these factors and use solar radio waves to forecast its future behavior. These techniques may also be applied to other data sets. Examples of these types of datasets include forecasting electrical power demands, modeling glucose dynamics, modeling and forecasting for Artificial Intelligence, modeling and forecasting of social data and graphs, modeling and forecasting of financial and economic data and modeling and forecasting of all systems that have time series data. Various examples of these are discussed more fully hereinbelow.

Prediction Using FPGA-Based AI or Artificial Neural Network

The above described technique is for the generation of an actuator for prediction of future behavior may be implemented within a field programmable gate array (FPGA) that performs the above described process in near real-time applications. By implementing the prediction techniques within an artificial intelligence implemented on an FPGA, future predictive behavior may be made by the AI based upon data that is currently being input in order to create the attractor for predicting the behavior in a near real-time manner.

Chaotic oscillators generate chaotic time series that can be highly unpredictable, and which unpredictability can be quantified by determining their maximum Lyapunov exponent. Chaotic time series having high Lyapunov exponent values are more complex than chaotic time series having low values and therefore, when performing time series prediction of these kinds of signals, it becomes quite difficult to perform a long-term prediction. One can perform time series prediction of chaotic signals with different values of Lyapunov exponent by using an artificial neural network or artificial intelligence that is implemented in a field-programmable gate array (FPGA) as shown generally in FIG. 23.

Selection of hidden neurons, training algorithm, and architecture are critical to implementation of such a system within an FPGA. For instance, hidden neurons influence the error on the nodes to which their output is connected, and the accuracy of training is determined by the architecture, number of hidden neurons in hidden layer, kind of activation function, inputs, and updating of weights.

Figure 23:
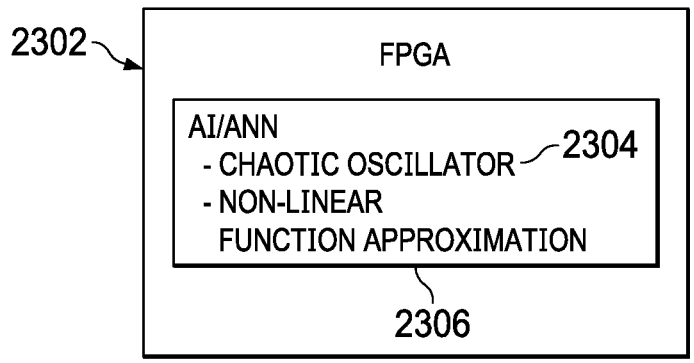
FIG. 23 illustrates an artificial neural network/AI implemented within a field programmable gate array (FPGA)

A chaotic time series may be generated in the following manner. A time series represents a measure of a physical variable $x_t$ registered at a time t, and it is discrete. The observed data can be used to model or to predict future values to determine the behavior of a time series. As shown in FIG. 23, a chaotic time series can be generated by implementing into an FPGA 2302 the chaotic oscillator 2304 described in say Rossler attractor, where x, y and z are state variables, and a, b, c, are real and positive coefficients. The chaotic oscillator 2304 would be implemented through a Artificial Intelligence or Artificial Neural Network 2306 within the FPGA 2302. The nonlinear function g(x) 2308 can be approached by piecewise-linear (PWL) functions.

Based on the approach introduced herein above an artificial neural network 2306 can be used taking advantage of their ability to approximate any nonlinear function. In addition, artificial neural network 2306 is characterized by fault tolerance, adaptivity, generalization, etc. Due to these characteristics, an artificial neural network 2306 is suitable for time series prediction, and we can implement it by using an FPGA 2302 due to its advantages for fast prototyping, configurability, re-programmability, and low development and acquisition costs.

Figure 24:
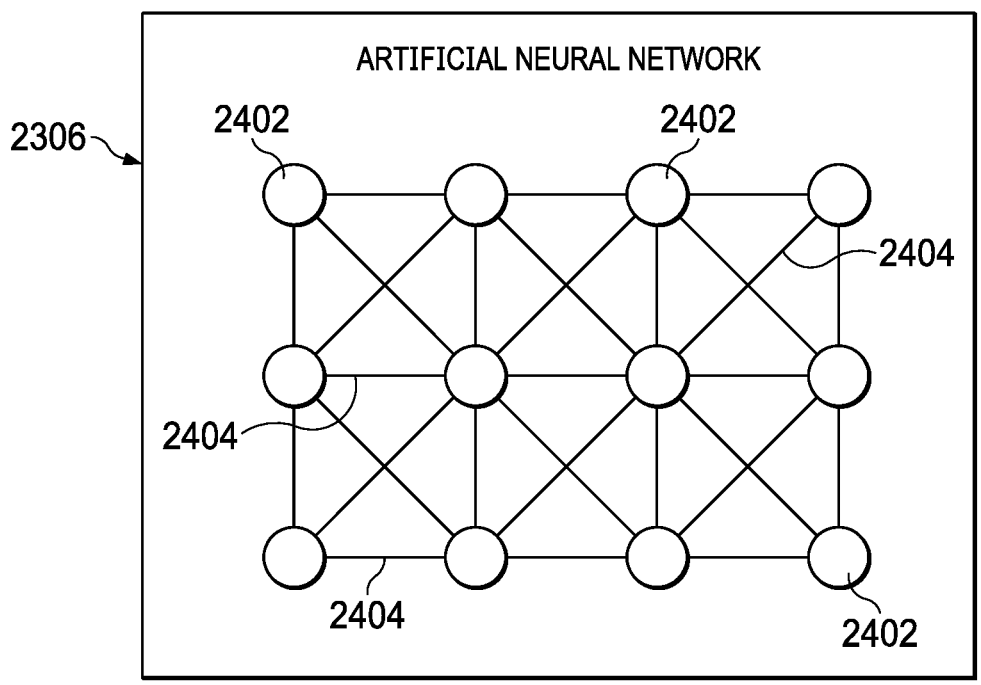
FIG. 24 illustrates an artificial neural network.

Referring now also to FIG. 24, an artificial neural network 2306 has elementary processing units called neurons or nodes 2402 whose processing capability is stored in the connections 2404 by synaptic weights, and whose adaptation depends on learning. Basically, there are three kinds of neurons: input neurons (that are used to allocate input values), hidden neurons (that are used to perform operations and consists of one or more layers), and output neurons (that are used to perform operations and to compare the values with target or reference ones). Where $x_j$ represents the input signals, w represents the synaptic weights (if w is positive it is associated to an excitation, if it is negative to an inhibition), b is the bias and $f$ denotes the activation function that defines the output of the neuron.

Figure 25:
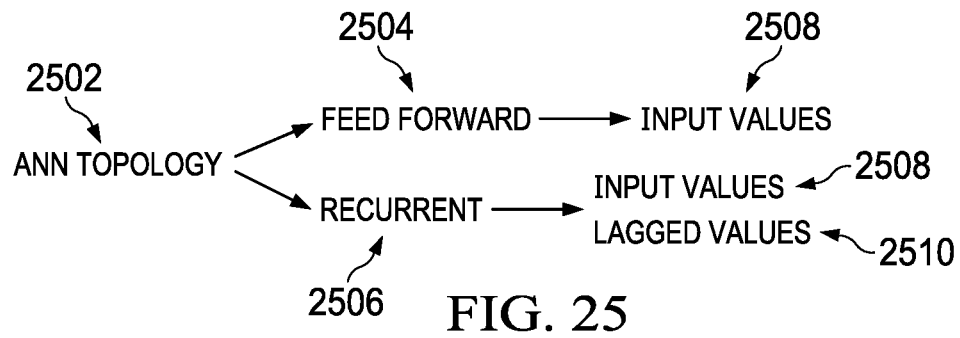
FIG. 25 illustrates the feedforward and recurrent topologies that may be associated with an artificial neural network.

Referring now to FIG. 25, among all types of artificial neural networks 2306, one can identify two major types of network topology 2502, namely: feedforward topology 2504 and recurrent topology 2506. A feedforward artificial neural network 2504 processes information in one direction, so that the prediction datum in y[k+1] depends only on the input values y[t] 2508 and cannot capture possible dependencies of y[k+1] on earlier values of y. A recurrent artificial neural network 2506 allows the neurons to depend not only on the input variables y[t] 2508, but also on their own lagged values 2510. Therefore, this kind of network builds a memory in the evolution of the neurons 2402. However, there is not a recipe on how many delay lines are required at the input layer to perform a good prediction.

Before implementing an artificial neural network 2306 into an FPGA 2302, one needs to train the topology for which a learning technique must be selected to adjust the parameters during the training processes. The learning technique can be supervised or unsupervised. The former does not involve competition, but it uses an external agent (actual output) for each input pattern that guides the learning process, in this case there is a teacher to provide feedback information. The unsupervised learning does not need a teacher to provide feedback for the information. In this case, the network discovers by itself patterns, features, regularities, correlations, or categories in the input data and code for them in the output.

Figure 26:
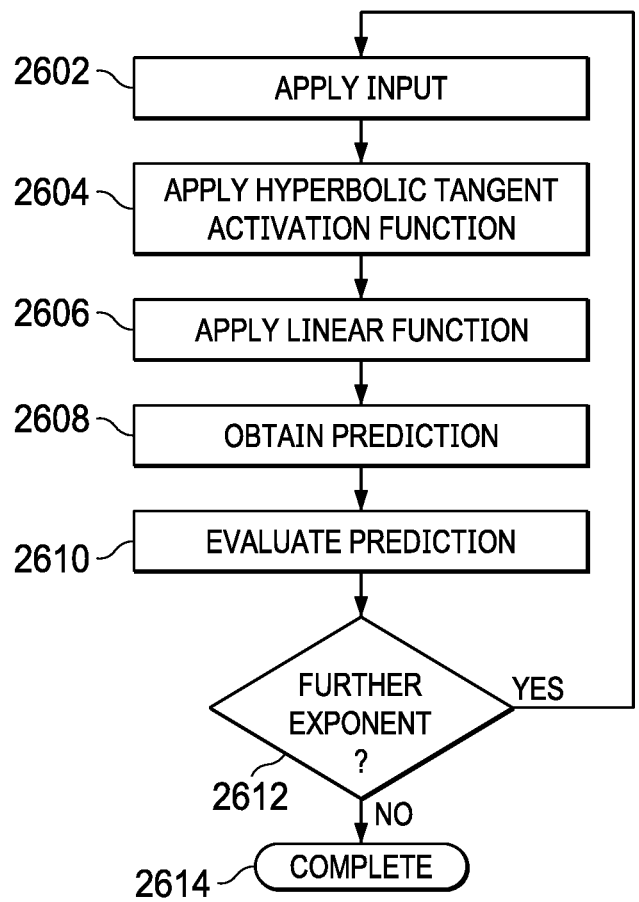
FIG. 26 illustrates a flow diagram of the process for training an artificial neural network.

As an example shown in FIG. 26, a feedforward artificial neural network can be trained using experimental data of the chaotic time series with different Lyapunov exponents. For the first five layers from the input at step 2602, a hyperbolic tangent activation function is applied at 2604 that can be implemented in digital hardware, and for the output layer a linear function is applied at 2606. The learning technique can be supervised and the weights for the input neurons can have a time delay line (y [k−1] . . . y[k−d]) to provide a finite dynamic response for the time series data at 2608. In this way, we can add tapped delay lines to perform better predictions. The prediction can be evaluated by measuring the MSE and RMSE at step 2610. Inquiry step 2612 determines if further Lyapunov exponents for the data exist for evaluation and if so, returns to step 2602 for processing with the further exponent. If no further exponents exist, the process is completed at 2614.

Schools of Machine Learning and Artificial Intelligence (AI)

Figure 27:
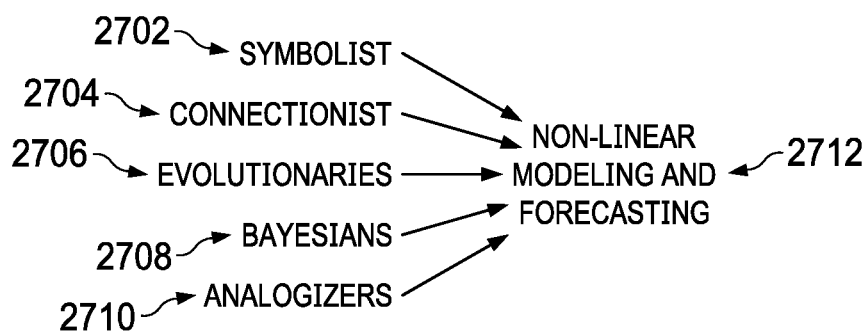
FIG. 27 illustrates various schools of machine learning.

Historically, there have been five schools of machine learning in industry. These schools include Symbolists 2702, Connectionists 2704, Evolutionaries 2706, Bayesians 2708, and Analogizers 2710. As shown in FIG. 27 each of these techniques may be implemented thru a nonlinear modeling and forecasting technique 2712 that enables implement all of the techniques together such that the types of data that are processed using each of these techniques may be processed using the nonlinear modeling and forecasting technique.

The symbolists school 2702 of machine learning focuses on inverse deduction or induction. Induction involves proving an individual instance to be true, and then showing that it is true for all other instances as well. This is the inverse of deduction in that deduction is based on a general principle to make a specific conclusion. The symbolists based system 2702 essentially works backwards to fill in the gaps in the system's knowledge. The origins are based on logic and philosophy. The implementation of this method can be seen in modern scientist robots because the method is very similar to the way real scientists work. Humans handle these robots to allow the robots to perform tasks that are much like modern human scientists.

The Connectionist school 2704 of machine learning "reverse engineers the brain" by creating artificial neurons so this technique obviously has its origins in neuroscience. The artificial neurons work by taking in inputs given individual weights. If the weighted inputs reach the threshold for a given neuron then the neuron will "fire" or send a 1. If the inputs do not reach the threshold then it will send a 0. Back propagation helps solve problems when error is introduced. Back propagation is the concept of which neuron needs to change and by how much to more accurately reflect the model. If a value of 1 should be seen at the output but only a value of 0.2 appears, then the error is valued as 0.8. This error value is compared to the weights of each input of the neuron as well as previous neurons in the network. This is executed all the way back to the initial inputs of the system and it is where we get the term backpropagation. This process of creating neural networks is called deep learning, and it is applied to areas of vision and image processing. It can also be found in Google's Cat Network that helps identify many images such as the human face and even cats. This method excels at allowing a computer to learn about a given set of information criteria.

This Evolutionaries school 2706 mimics evolution by constantly evolving and adapting to unknown conditions. The Evolutionaries technique 2706 models genes and DNA in the evolutionary process. Not only do they simulate evolution, but they are applied to modern day applications such as robotics. The performance data of such robots is carried over to the next model as a kind of "robot selection." This approach is similar to selective breeding and results in very robust outcomes because there have been many trials of the model beforehand. John Holland was a very prominent name for Evolutionaries 2706 and continues to be even after his death in 2015. Holland was a pioneer in genetics algorithms in computer science and created a foundational "fundamental theorem in genetics algorithm." 3D printing and bioinformatics are also areas that are carried out by those in the Evolutionaries school 2706.

The Bayesian school 2708 handles uncertainty with probabilistic interference and has an origin in statistics. This method starts off with an initial hypothesis and then updates your belief in each hypothesis based on incoming evidence. Eventually the system will end up with a hypothesis that is more likely than the others. Self-driving cars and spam filtering are one of the main users of Bayesian inference 2708. The initial hypothesis is called a prior. Data is obtained, and the prior is updated based on the data. The outcome is called a posterior and the posterior is updated with more data to become a prior again. The method is repeated until an outcome is produced.

The Analogizers school 2710 of thought matches bits of data together through analogy. This may seem like a simple approach, but it is actually similar to the neural networks methods because of its nearest neighbor principle. An example of this nearest neighbor approach is the technology applied to Netflix movie ratings. Users with similar ratings will get similar recommendations based on these reviews.

Assisted AI Summary

Figure 28:
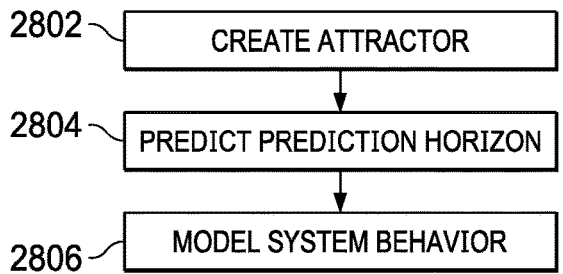
FIG. 28 illustrates a process for modeling system behavior from an attractor.

Each of the above described systems can solve a specific problem better than the other four systems, and it is best to combine all of systems for maximum effectiveness. Each school of thought has its own master algorithm. The challenge is to design a master algorithm that will solve all the problems that each school aims to resolve. Attractor assisted AI such as that disclosed above combines the benefits of all these approaches. This method illustrated in FIG. 28 uses the drivers of a dynamical system to create an attractor at step 2802 that can predict up to a value of T at step 2804 that is the prediction horizon to enhance machine learning methods by making them faster and using less training data. This enables modeling of the behavior of a system at step 2806 using an attractor in terms of some invariants directly extractable from the system's dynamics, without reference to any underlying dynamics. The value of T is the forecasting window for all systems and serves as the horizon to which a prediction can be accurately approximated. A larger data set will increase the forecasting capabilities up to a value of T which is the forecasting window. Any prediction beyond $T_{max}$ is no more accurate than a statistical model. This attractor method benefits form the use of a Graphics Processing Unit (GPU) because it requires many simultaneous calculations. The GPU is used to generate an attractor that can be used to predict non-linear systems more accurately than a statistical method that can then be implemented into an artificial intelligence for use with machine learning. The implementation of all five methods of machine learning into one method makes attractor assisted AI the master algorithm for machine learning as a unified theory of machine learning.

Photonic Reservoir Computing

Reservoir Computing (RC) is a set of machine learning methods for designing and training artificial neural networks. RC is a framework for computation that may be viewed as an extension of neural network. Typically an input signal is fed into a fixed (random) dynamical system called a reservoir and the dynamics of the reservoir map the input to a higher dimension, and a simple readout mechanism is trained to read the state of the reservoir and map it to the desired output. The main benefit is that training is performed only at the readout stage and the reservoir is fixed. The reservoir consists of a collection of recurrently connected units. The connectivity structure is usually random, and the units are usually nonlinear. The overall dynamics of the reservoir driven by the input, and is also affected by the past. A rich collection of dynamical input-output mapping is a crucial advantage over time delay neural networks. The idea behind these techniques is that one can exploit the dynamics of a recurrent nonlinear network to process time series without training the network itself, but simply adding a general linear readout layer and only training the latter. This results in a system that is significantly easier to train (the learning is reduced to solving a system of linear equations), yet powerful enough to match other algorithms on a series of benchmark tasks. Thus, the implementation leverages the dynamics of the nonlinearity to process time series without training the network itself. The attractor of any time series with a photonic reservoir is modeled in a similar manner to how turbulent dynamo and the attractor of flux signals are modeled. RC has been successfully applied to, for instance, channel equalization, speech recognition and won an international competition on prediction of future evolution of financial time series.

Reservoir Computing enables efficiently implementation of simplified recurrent neural networks in hardware, such as e.g. optical components. Optical computing has been investigated for decades as photons propagate faster than electrons, without generating heat or magnetic interference, and thus promise higher bandwidth than conventional computers. The photonic approach is notably different from the state-of-the-art electronic brain simulators, such as the Neurogrid from Stanford University and the SyNAPSE from IBM. It is also less complex than recent hardware implementations of spiking networks, since the reservoir is composed of simple analog neurons. Thus, RC would enable building of high-speed and energy efficient photonic devices.

The potential of these RC systems can be significantly increased by feeding the output signal back into the reservoir. It has been shown that this additional feedback allows the algorithm to solve long horizon prediction tasks, such as forecasting chaotic time series, which are impossible to solve otherwise. The use of feedback would also allow the setup to run autonomously. This would provide the system with the ability to produce an output signal without receiving any input signal, and thus make the system capable of generating a periodic time series. Implementing this idea experimentally requires, in principle, a sufficiently fast readout layer capable of generating and feeding back the output signal in real-time (analog).

Figure 29:
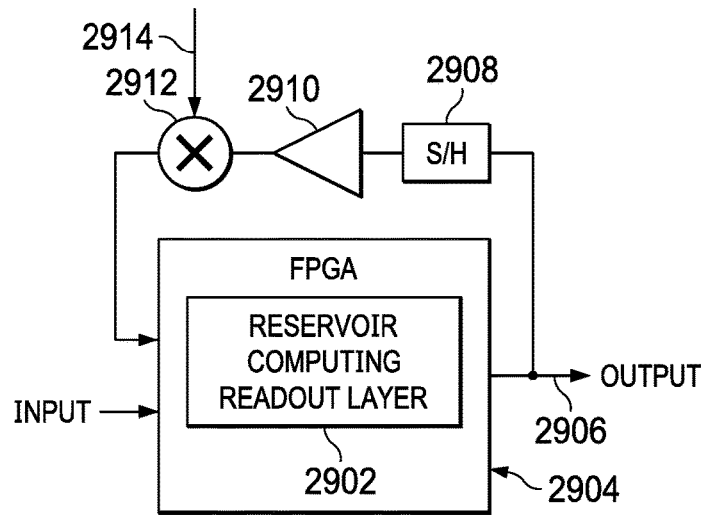
FIG. 29 illustrates a photonic reservoir system with output feedback.

Referring now to FIG. 29, there is illustrated a photonic reservoir system with an output feedback. The readout layer of the opto-electronic reservoir 2902, can be implemented on an FPGA 2904. The use of high-speed dedicated electronics makes it possible to compute the output signal 2906 in real time, and thus feed it back into the reservoir 2902. This results in a digital readout layer, that nevertheless allows one to investigate many of the issues that will affect a system with purely analogue feedback. Using analog output layers for output feedback would require adding an additional electronic circuit consisting of a sample and hold circuit 2908, amplification 2910, and multiplication 2912 by the input mask 2914. Such a two-step procedure, in which part of the experiment is analog and part digital, is a natural procedure.

Extreme Learning Machine

Extreme learning machines are feedforward neural networks for classification, regression, clustering, sparse approximation, and feature learning with a single layer or multiple layers of hidden nodes, where the parameters of hidden nodes (not just the weights connecting inputs to hidden nodes) need not be tuned. These hidden nodes can be randomly assigned and never updated (i.e. they are random projection but with nonlinear transforms), or can be inherited from their ancestors without being changed. In most cases, the output weights of hidden nodes are usually learned in a single step, which essentially amounts to learning a linear model.

In most cases, ELM is used as a single hidden layer feedforward network (SLFN) including but not limited to sigmoid networks, RBF networks, threshold networks, fuzzy inference networks, complex neural networks, wavelet networks, Fourier transform, Laplacian transform, etc. Due to its different learning algorithm implementations for regression, classification, spare coding, compression, feature learning and clustering, multi ELMs have been used to form multi hidden layer networks, deep learning or hierarchical networks. A hidden node in ELM is a computational element, which need not be considered as classical neuron. A hidden node in ELM can be classical artificial neurons, basis functions, or a subnetwork formed by some hidden nodes.

A Feedforward neural network, such as a back-propagation (BP) neural network, is a good method for time series prediction. But for traditional feedforward neural networks, there are some limitations which have a negative effect on the application of these neural networks (local minimum, high computation complexity, slow convergence speed . . . etc.). To overcome these problems, extreme learning machine (ELM) can be used based on a Penrose generalized inverse matrix. For ELM, there are random allocations for input weights and thresholds, and the output weights can be worked out just by one step. Therefore, the ELM only needs to determine the number of hidden layer nodes. But an appropriate number of hidden layer nodes are difficult to be determined. When the number of hidden layer nodes is small, ELM may not be able to effectively study the samples. But when the number of hidden layer nodes is large, it will enlarge the computation complexity and even result in overfitting for ELM. Therefore, to improve the prediction performance and generalization performance, it is important to eliminate the influence of hidden layer nodes to prediction or choose an appropriate number of hidden layer nodes.

There is a fast-pruned extreme learning machine (P-ELM) that was applied to classification successfully. There is also an optimally pruned extreme learning machine (OP-ELM). These methods all try to get the optimal number of hidden layer nodes using a pruning method. However, for a pruning method, it is difficult to determine the initial size of the neural networks. And it is always common to start with a larger size initial neural network in order to provide better prediction accuracy. So, the computational complexity is always high and the training time is also large. There are also methods with an incremental extreme learning machine (I-ELM) based on enhanced random search. For example, there are proposals with an error minimized extreme learning machine (EM-ELM) based on the growth of hidden nodes and incremental learning. These methods both try to get the optimal number of hidden layer nodes by a growing method. But for a growing method, with the increase of hidden layer nodes, the output weights should be recalculated. So, a growing method also greatly enlarges the computation complexity of ELM.

These methods all try to eliminate the influence of hidden layer nodes to prediction by getting the optimal number of hidden layer nodes, but the computation complexity is always high. There are still proposals that try to solve the problem by other ways such as a kernel method. In this method, kernel function is used to build the nonlinear mapping, and the number of hidden layer nodes does not need to be selected. So, the kernel method can overcome the influence of the hidden layer nodes for prediction. But for different kernel functions, they have different characteristics, and the performances are different with different datasets.

Figure 30:
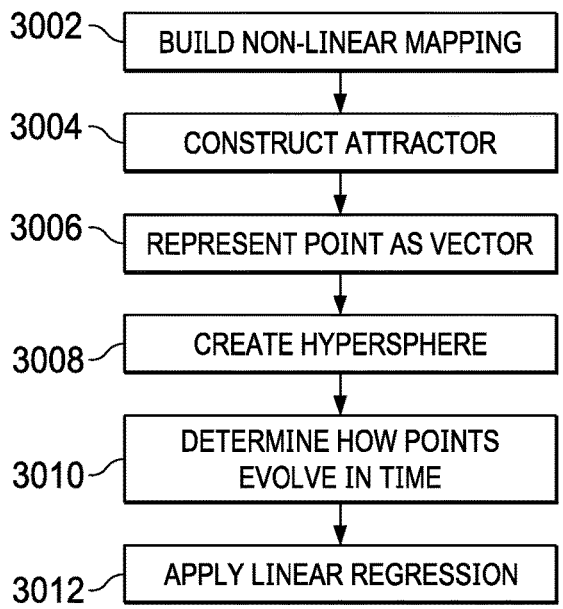
FIG. 30 illustrates a flow diagram of a process for providing an improved extreme learning machine.

Therefore, to overcome the influence of a large number of hidden layer nodes for prediction and to enhance the prediction performance of ELM, an improved ELM is proposed based on orthogonal projections to a latent structures method. The improved ELM can have the steps as more fully illustrated in FIG. 30. Firstly, the hidden layer of ELM is used to build the nonlinear mapping for input variables at step 3002 and generate the output matrix H, where the number of bidden layer nodes can be randomly assigned. The output matrix generation is accomplished by first using a Delay Embedding technique to construct the attractor of the dynamics at step 3004. This requires an optimum delay to be used using minima of the mutual information. The last point in the data time series will be somewhere on the surface of the reconstructed attractor. That point can be represented as a vector in the multi-dimensional embedding space (connecting the origin to that point with a vector |P> (p for present) at step 3006. This vector has the same dimension (components) as the embedding dimension. Each embedding dimension represents a driver of the dynamics. For a selected present point on the attractor (the end point of vector |p>), a hypersphere is created at step 3008 around the point and then a determination is made at step 3010 of how other points in the hypersphere evolve in time. The matrix of evolution of these points corresponds to the matrix H. Linear regression is then applied by applying the matrix H to vector |p> at step 3012. The outcome comprises a vector for a future state vector |P>. k This approach corresponds to a nonlinear regression. Compared with least squares regression, the orthogonal technique can reduce the high dimensions, overcome the multicollinearity among H, which are caused by an improper number of hidden layer nodes.

Nonlinear dynamics are an effective tool for the analysis of time series data. The chief difficulty in applying these techniques to real data has been the lack of good criteria for the selection of the time delay required for optimal embedding of the data in phase-space. A specific technique is presented herein for this selection based on the mutual information for the time series. The selection works well for model systems and is now being used to reconstruct the dynamics for other data sets. The technique of attractor reconstruction (Ruelle, Takens, and Packard) has been applied to the $F_{10.7}$ time series. The resulting attractor has been used to make forecasts of future data.

The forecasts must be tuned to take into account the dimension of the system defined by the reconstructed attractor and the Lyapunov exponent for the system. In addition, techniques that forecast the phasing of the extremas of the variations should be examined.

In addition to the efforts described herein, several tasks can further enhance forecasting techniques. These tasks include the following: noise reduction using the nonlinear techniques developed by Kostelich and Yorke, (E. J. Kostelich and J. A. Yorke, "Noise Reduction: Finding the Simplest Dynamical System Consistent with the Data," *Physica* D 41, 183, (1990), which is incorporated herein by reference), and the more recent technique developed by Sauer (T. Sauer, "A Noise Reduction Method for Signals from Nonlinear Systems," *Physica* D 58, 193, 1992, which is incorporated herein by reference) accurate calculation of the dynamical invariants of the attractor like the Badii-Politi dimension (R. Badii and A. Politi, *J. Stat. Phys.* 40, 725 (1985), which in incorporated herein by reference) of the system (needed to determine the forecast horizon); and the development of the optimal linear association method pioneered by Jimenez and Moreno as described in J. Jimenez and J. Moreno, *Phys. Rev. A.*, 45, 3553, March 1992 which is incorporated herein by reference.

Finally, connections between the nonlinear models and the physics of the time series can be used to for example fit ordinary differential equations to chaotic data. Baake has introduced a technique by which one can treat the problem of fitting ordinary differential equations to chaotic data using boundary value methods as described in E. Baake et al., "Fitting Ordinary Differential Equations to Chaotic Data," *Phys. Rev. A*, 45, 1985 which is incorporated herein by reference. Ashrafi and Roszman have constructed a canonical transformation that can transform the dynamo equations to the established Lorenz form as shown in S. Ashrafi and L. Roszman, Solar Flux Forecasting Using Mutual Information with Optimal Delay, AAS 93-311, Spaceflight Dynamics 1993, American Astronautical Society Publication, Advances in the Astronautical Sciences, Volume 84 Part II pages 901-913. The Lorenz equations have been studied in great detail in the chaos literature.

Heart Monitoring Application

The attractor assisted AI techniques described herein above may be used for analyzing the nonlinear features, topological features and dynamical invariants of Heart Rate Variability (HRV) of the electrocardiogram (ECG) signal. By combining this ECG signal analysis with a time-bandwidth analysis of the ECG signal, prediction of heart attacks or other heart irregularities may be better provided.

The most common cause of sudden cardiac death (SCD) in adults over the age of 30 is coronary artery atheroma. The most common finding at postmortem examination is chronic high-grade stenosis of at least one segment of a major coronary artery, the arteries which supply the heart muscle with its blood supply. A significant number of cases also have an identifiable clot in a major coronary artery which causes transmural occlusion of that vessel. Left ventricular hypertrophy is the second leading cause of sudden cardiac death in the adult population. This is most commonly the result of longstanding high blood pressure which has caused secondary damage to the wall of the main pumping chamber of the heart, the left ventricle. Hypertrophy, as well, is associated with cardiac arrhythmias.

The mechanism of death in most patients dying of sudden cardiac death is ventricular fibrillation; therefore, there may be no prodromal symptoms associated with the death. Patients may be going about their daily business and suddenly collapse, without any typical features of myocardial infarction (heart attack) like chest pain or shortness of breath. However, it may abruptly strike any person if he or she possesses of high-risk heart disease, even young persons, and athletes. Besides utilizing public access defibrillation (PAD) procedure to rescue impending death patient after collapse, the better way is to prevent onset SCD by adopting medical aid prior to collapse. Thus, is it possible to generate an early warning, even before a crisis. Researchers have found that the respiratory peak of the heart rate variability (HRV) in SCD patient can disappear during the nighttime one-week before death. They had observed that HRV is low in patients who experience SCD and is high in young healthy subjects.

Though the relationship between short-term HRV and SCD is unknown, it seems repolarization alternans phenomena provides a safe, noninvasive marker for the risk of SCD, and has proven equally effective to an invasive and more expensive procedure, invasive electrophysiological study (EPS), which is commonly used by cardiac electrophysiologists. Analysis of heart rate variability (HRV) has provided a non-invasive method for assessing cardiac autonomic control. HRV is generally accepted as a strong and independent predictor of mortality after an acute myocardial infarction, such that a reduced HRV is associated with a higher risk for severe ventricular arrhythmia and sudden cardiac death. Although until now different Linear methods have been used for analysis of an HRV signal, here a nonlinear attractor reconstruction which provides more information than Linear methods. In addition, researchers have shown that classic Linear methods do not have enough ability to predict the SCD.

Figure 31:
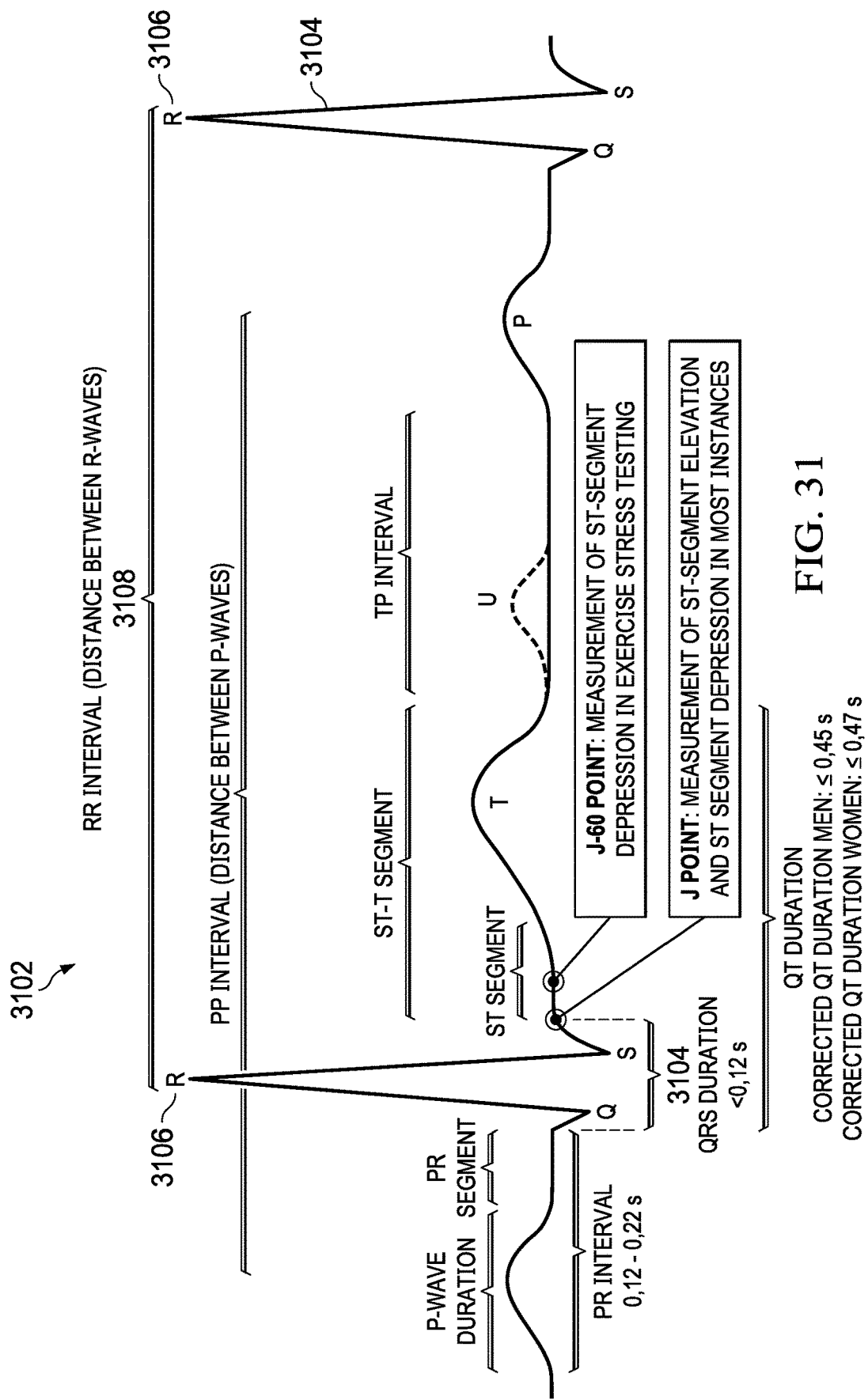
FIG. 31 illustrates an electrocardiogram signal.

Referring now to FIG. 31, there is illustrated an ECG signal 3102. The QRS-complexes 3104 in the ECG-signal 3102 can be detected from which the RR-intervals and HRV signal (R 3106 is a point corresponding to the peak of the QRS complex 3104 of the ECG wave; and RR is the interval 3108 between successive Rs can be determined. The term NN can be used in place of RR to emphasize the fact that the processed beats are normal beats). The preprocessed HRV signal can be used to extract features from it.

Figure 32:
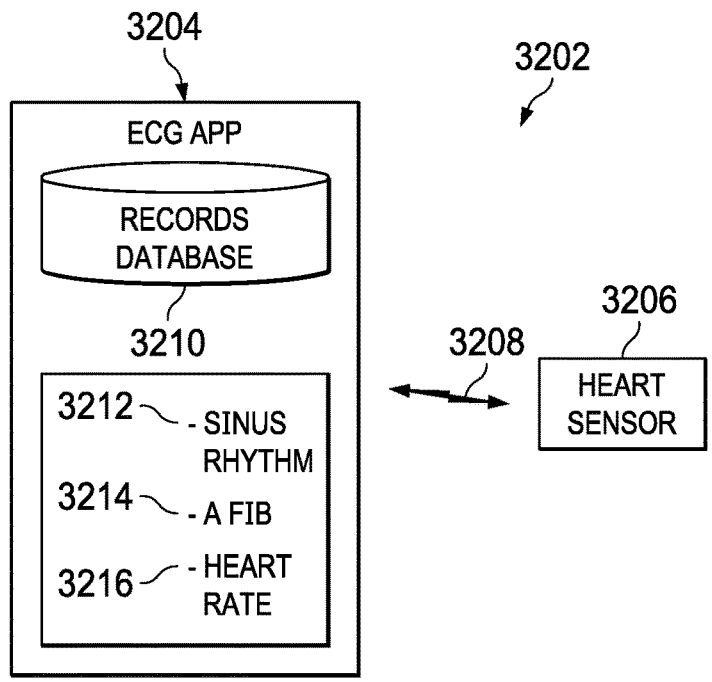
FIG. 32 illustrates a heart monitoring system.

Referring now to FIG. 32, there is illustrated a heart monitoring system 3202. The heart monitoring system 3202 records heart beats using an ECG application 3204 implemented for example on a smart phone or smart watch such as an iPhone® or Apple® Watch. The heartbeats are received from a heart sensor 3206 over a connection 3208 that may be either wired or wireless and are stored in a records database 3210. An electrocardiogram (also called an ECG or EKG) is a test that records the timing and strength of the electrical signals that make the heartbeat. By looking at an ECG, a doctor can gain insights about heart rhythm and look for irregularities.

The ECG app 3204 records heartbeat and rhythm using the electrical heart sensor 3206 that may be a part of the monitoring device such as an Apple® Watch Series 4 or a separate sensor. The ECG application 3204 checks the recording for atrial fibrillation (AFib), a form of irregular rhythm. The ECG app 3204 records an electrocardiogram which represents the electrical pulses that make a heartbeat for storage in the database 3210. The ECG app 3204 checks these pulses to get heart rate and see if the upper and lower chambers of the heart are in rhythm. If they're out of rhythm, that could be AFib.

The ECG signal can monitor a number of parameters with respect to a heartbeat. A sinus rhythm result 3212 indicates if the heart is beating in a uniform pattern between 50 and 100 BPM. This happens when the upper and lower chambers of the heart are beating in sync. A sinus rhythm result 3212 only applies to that particular recording and doesn't mean your heart beats with a consistent pattern all the time. It also does not mean that you're healthy.

An AFib result 3214 means the heart is beating in an irregular pattern between 50 and 120 BPM. AFib 3214 is the most common form of serious arrhythmia, or irregular heart rhythm. If you receive an AFib 3214 classification and you have not been diagnosed with AFib, you should talk to your doctor.

A heart rate 3216 under 50 BPM or over 120 BPM affects the ECG app's 3204 ability to check for AFib 3214, and the recording is considered inconclusive. A heart rate 3216 can be low because of certain medications or if electrical signals are not properly conducted through the heart. Training to be an elite athlete can also lead to a low heart rate. A high heart rate could be due to exercise, stress, nervousness, alcohol, dehydration, infection, AFib, or other arrhythmia.

The ECG app 3204 on the monitoring device generates an ECG signal that is similar to a single-lead (or Lead I) ECG. In a doctor's office, a standard 12-lead ECG is usually taken. This 12-lead ECG records electrical signals from different angles in the heart to produce twelve different waveforms. The ECG app 3204 on the monitoring device measures a waveform similar to one of those twelve waveforms. A single-lead ECG is able to provide information about heart rate and heart rhythm and enables classification of AFib 3214. However, a single-lead ECG cannot be used to identify some other conditions, like heart attacks. Single-lead ECGs are often prescribed by doctors for people to wear at home or within the hospital so that the doctor can get a better look at the underlying rate and rhythm of the heart. However, the ECG app 3204 on the monitoring device allows you to generate an ECG similar to a single-lead ECG without a prescription from your doctor.

In studies comparing the ECG app 3204 on a monitoring device to a standard 12-lead ECG taken at the same time, there was agreement between the ECG app classification of the rhythm as sinus or AFib 3214 compared to the standard 12-lead ECG.

The ability of the ECG app 3204 to accurately classify an ECG according to AFib 3214 and sinus rhythm 3212 was tested in a clinical trial of approximately 600 subjects, and demonstrated 99.6% specificity with respect to sinus rhythm classification and 98.3% sensitivity for AFib classification for the classifiable results. The clinical validation results reflect use in a controlled environment. Real world use of the ECG app 3204 may result in a greater number of strips being deemed inconclusive and not classifiable.

Current claims with respect to the ECG app 3204 within a monitoring device such as the Apple Watch Series 4® include 1) the ECG app cannot detect a heart attack; 2) the ECG app cannot detect blood clots or a stroke; and 3) the ECG app cannot detect other heart-related conditions. These include high blood pressure, congestive heart failure, high cholesterol, or other forms of arrhythmia.

Figure 33:
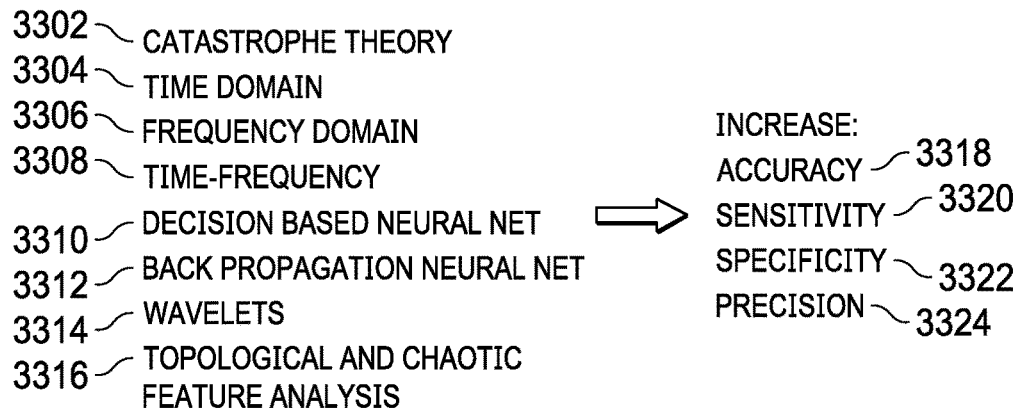
FIG. 33 illustrates the manner for combining multiple analysis techniques for analyzing an electrocardiogram signal.
Figure 34:
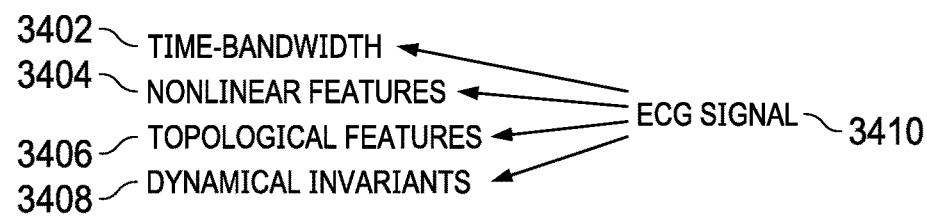
FIG. 34 illustrates a further technique for combining heart signal analysis processes for analyzing electrocardiogram signal.

The system described herein improves the operation of the ECG app 3204 using topological features of the attractor that can help identify deterioration of heart function. Using additional techniques for analyzing the ECG signal as described herein below prediction of deteriorating heart efficiency as well as sudden cardiac death is possible. As shown in FIG. 33, by combining the techniques of Catastrophe theory 3302, time domain 3304, frequency domain 3306, time-frequency 3308, decision based neural net 3310, back propagation neural net 3312, wavelets 3314, as well as topological and chaotic feature analysis 3316 to increase accuracy (AC) 3318, sensitivity (SN) 3320, specificity (SP) 3322 and precision (P) 3324. These deaths can be reduced by using medical equipment, such as defibrillators, after detection by the improved ECG app 3204. However, a simple inspection of the ECG signal cannot extract proper information in the signal to predict deterioration of heart health and sudden cardiac death. There is a need for a way to predict such deterioration of heart and the possibility of a catastrophic sudden cardiac death far enough ahead of time for the patient to get to a hospital. This is achieved by leveraging techniques using on Attractor Assisted AI as described in U.S. patent application Ser. No. 16/161,840, entitled UNIFIED NONLINEAR MODELING APPROACH FOR MACHINE LEARNING AND ARTIFICIAL INTELLIGENCE (ATTRACTOR ASSISTED AI), filed Oct. 16, 2018, which is incorporated herein by reference in its entirety, as well as Multiple Layer Overlay Modulation as described in U.S. Pat. No. 8,503,546, entitled MULTIPLE LAYER OVERLAY MODULATION, filed Jan. 31, 2008, and issued Aug. 6, 2013, which is incorporated herein by reference in its entirety. As shown in FIG. 34, using techniques described in these two patents, an improved ECG app can extract Time-Bandwidth 3302 and the nonlinear features 3304, topological features 3306 and dynamical invariants 3308 from the HRV of an ECG signal 3310. Finally, healthy people and people at risk of sudden cardiac death can be classified by such time-bandwidth and topological features. It seems that HRV signals have special features in the vicinity of the occurrence of SCD that can distinguish between patients prone to sudden cardiac death and normal people. The techniques introduced here can be incorporated into wearable devices such as watches with biometric sensors (i.e. Apple® watch can monitor ECG signals and over 30 countries are able to use this feature).

Figure 35:
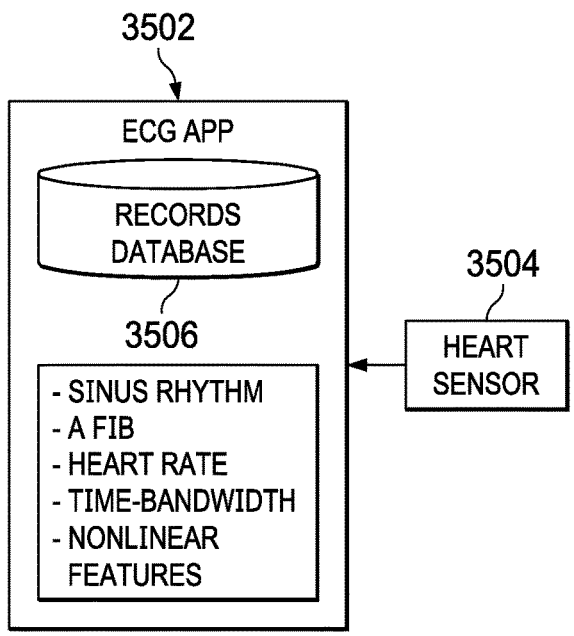
FIG. 35 illustrates a block diagram of an electrocardiogram application with associated heart sensor.

Referring now to FIG. 35, there is illustrated a further embodiment of a block diagram of an ECG application 3502 and associated heart sensor 3504. The configuration is similar to that disclosed in FIG. 32 and includes a record database 3206 and various functionalities. These functionalities include sinus rhythm 3508, AFib monitoring 3510, heart rate monitoring 3512, time bandwidth analysis 3514 and nonlinear features analysis 3516. The sinus rhythm 3508, aFib monitoring 3510, heart rate monitoring 3512 operate in the same manner as those described previously and the time bandwidth analysis 3514 and nonlinear features analysis 3516 will be more fully described hereinbelow.

Time-Bandwidth Product

A normal heart is an efficient electromechanical and biological system that has minimum time-bandwidth product associated with ECG signals reflecting the hearts operation. As the heart becomes unhealthy for any reasons, its efficiency reduces with increasing the time-bandwidth product of its ECG signals. To be able to leverage time-bandwidth product as a biological marker for a healthy heart, it would be convenient to express signal amplitude s(t) in a mathematically complex form. Note that s(t) could be an ECG, HRV or any other signal structure including RR(t), PR(t) or any combinations in PQRSTU signals.

Therefore, the complex signal can be represented as:

$$\Psi(t) = s(t) + j\sigma(t)$$

Where $s(t) \equiv$ real signal $\sigma(t) \equiv$ imaginary signal (quadrature)

$$\sigma(t) = \frac{1}{\pi}\int_{-\infty}^{\infty} s(\tau)\frac{d\tau}{\tau - t}$$

$$s(t) = -\frac{1}{\pi}\int_{-\infty}^{\infty} \sigma(t)\frac{d\tau}{\tau - 1}$$

Where s(t) and σ(t) are Hilbert transforms of one another and since σ(t) is the quadrature of s(t), they have similar spectral components. That is if they were the amplitudes of soundwaves, the ear could not distinguish one form from the other.

Let us also define the Fourier transform pairs as follows:

$$\Psi(t) = \frac{1}{\pi}\int_{-\infty}^{\infty} \varphi(f)_{e^{j\omega t}df}$$

$$\varphi(f) = \frac{1}{\pi}\int_{-\infty}^{\infty} \Psi(t)_{e^{-j\omega t}dt}$$

$$\Psi^*(t)\Psi(t) = [s(t)]^2 + [\sigma(t)]^2 + \ldots \equiv \text{signal power}$$

Let's also normalize all moments to $M_0$ $$M_0 = \int_0^\tau s(t)\,dt$$

$$M_0 = \int_0^\tau \varphi^*\varphi\,df$$

Then the moments are as follows:

$$M_0 = \int_0^\tau s(t)\,dt$$

$$M_1 = \int_0^\tau ts(t)dt$$

$$M_2 = \int_0^\tau t^2 s(t)dt$$

$$M_{N-1} = \int_0^\tau t^{N-1} s(t)dt$$

In general, one can consider the signal s(t) be represented by a polynomial of order N, to fit closely to s(t) and use the coefficient of the polynomial as representation of data. This is equivalent to specifying the polynomial in such a way that its first N "moments" Mj shall represent the data. That is, instead of the coefficient of the polynomial, the moments can be used. Another method is to expand the signal s(t) in terms of a set of N orthogonal functions φk(t), instead of powers of time. Here, the data is considered to be the coefficients of the orthogonal expansion. One class of such orthogonal functions are sine and cosine functions (like in Fourier series).

Therefore, the above moments are represented using the orthogonal function w with the following moments:

$$\bar{t} = \frac{\int \psi^*(t)t\psi(t)dt}{\int \psi^*(t)\psi(t)dt}$$

$$\overline{t^2} = \frac{\int \psi^*(t)t^2\psi(t)dt}{\int \psi^*(t)\psi(t)dt}$$

$$\overline{t^n} = \frac{\int \psi^*(t)t^n\psi(t)dt}{\int \psi^*(t)\psi(t)dt}$$

Similarly:

$$\bar{f} = \frac{\int \varphi^*(f)f\varphi(f)df}{\int \varphi^*(f)\varphi(f)df}$$

$$\overline{f^2} = \frac{\int \varphi^*(f)f^2\varphi(f)df}{\int \varphi^*(f)\varphi(f)df}$$

$$\overline{f^n} = \frac{\int \varphi^*(f)f^n\varphi(f)df}{\int \varphi^*(f)\varphi(f)df}$$

If complex signal are not used, then $$\bar{f} = 0$$

To represent the mean values from time to frequency domains, replace $$\Psi(t) \rightarrow \varphi(f)$$

$$t \rightarrow -\frac{1}{2\pi j}\frac{d}{df}$$

Conversely to represent the mean values from frequency to time domains, replace $$\varphi(f) \rightarrow \Psi(t)$$

$$f \rightarrow \frac{1}{2\pi j}\frac{d}{dt}$$

These are equivalent to somewhat mysterious rule in quantum mechanics where classical momentum becomes an operator $$P_x \rightarrow \frac{h}{2\pi j}\frac{\partial}{\partial x}$$

Therefore, using the above substitutions:

$$\bar{f} = \frac{\int \varphi^*(f) f \varphi(f) df}{\int \varphi^*(f) \varphi(f) df}$$

$$= \frac{\int \psi^*(t) \left(\frac{1}{2\pi j}\right) \frac{d\psi(t)}{dt} dt}{\int \psi^*(t) \psi(t) dt}$$

$$= \left(\frac{1}{2\pi j}\right) \frac{\int \psi^* \frac{d\psi}{dt} dt}{\int \psi^* \psi dt}$$

And $$\bar{f^2} = \frac{\int \varphi^*(f) f^2 \varphi(f) df}{\int \varphi^*(f) \varphi(f) df}$$

$$= \frac{\int \psi^* \left(\frac{1}{2\pi j}\right)^2 \frac{d^2}{dt^2} \psi dt}{\int \psi^* \psi dt}$$

$$= -\left(\frac{1}{2\pi}\right)^2 \frac{\int \psi^* \frac{d^2}{dt^2} \psi dt}{\int \psi^* \psi dt}$$

$$\bar{t^2} = \frac{\int \psi^* t^2 \psi dt}{\int \psi^* \psi dt}$$

An effective duration and effective bandwidth is defined as:

$$\Delta t = \sqrt{2\pi \overline{(t-\bar{t})^2}} = 2\pi \cdot \text{rms in time}$$

$$\Delta f = \sqrt{2\pi \overline{(f-\bar{f})^2}} = 2\pi \cdot \text{rms in frequency}$$

But knowing that $$\overline{(t-\bar{t})^2} = \bar{t^2} - (\bar{t})^2$$

$$\overline{(f-\bar{f})^2} = \bar{f^2} - (\bar{f})^2$$

The equations can be simplified by making the following substitutions $$\tau = t - \bar{t}$$

$$\Psi(\tau) = \psi(t) e^{-j\bar{\omega}\tau}$$

$$\omega_0 = \bar{\omega} = 2\pi \bar{f} = 2\pi f_0$$

It is also known that $$(\Delta t)^2 (\Delta f)^2 = (\Delta t \Delta f)^2$$

and therefore $$(\Delta t \Delta f)^2 = \frac{1}{4}\left[4 \frac{\int \Psi^*(\tau) \tau^2 \Psi(\tau) d\tau \int \frac{d\Psi^*}{d\tau} \frac{d\Psi}{d\tau} d\tau}{\left(\int \Psi^*(\tau) \Psi(\tau) d\tau\right)^2}\right] \geq \left(\frac{1}{4}\right)$$

$$(\Delta t \Delta f) \geq \left(\frac{1}{2}\right)$$

Now instead of $$(\Delta t \Delta f) \geq \left(\frac{1}{2}\right)$$

This value can be determined for healthy individuals as well as unhealthy and the ones prone to sudden cardiac death (SCD). The determined values can then be compared to monitored ECG signal to detect potential heart health conditions.

This time-bandwidth product can be a biomarker for detection of issues, degradation of efficient heart function as well as prediction of SCD. As the heart health deteriorates, the time-bandwidth product increases to a new value from its more efficient healthy minimum.

Topological and Chaotic Features Analysis

Figure 36:
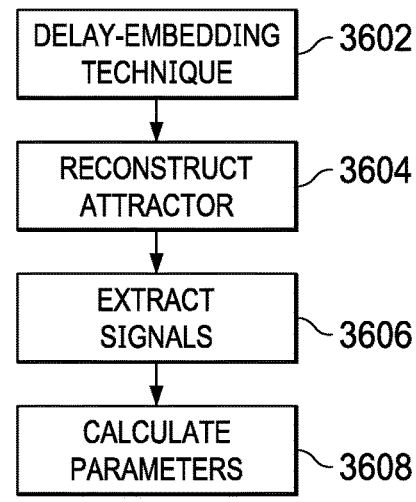
FIG. 36 illustrates a process for analyzing topological and chaotic features within an electrocardiogram signal.

In the next step, Attractor Assisted AI techniques as described herein above are leveraged in analyzing the ECG signal. As shown in FIG. 36 the process for analyzing topological and chaotic features starts by using delay-embedding techniques at step 3602 to help analyze a time series and to reconstruct the attractor directly from the time series at step 3604. The time series could be any combination of PQRSTU signals. That is signals can be extracted at step 3606 such as PQ, QR, RS, ST and TU as well as PP, QQ, RR, SS, TT, UU as shown in FIG. 31 or any other permutation as the signal. A number of parameters can then calculate at step 3608. These parameters include:

The embedding dimension of the attractor that gives us the causal drivers of such dynamics The attractor dimension which would be fractional (fractal)

The Correlation dimensions

The Lyapunov exponent

The Kolmogorov Entropy

The Mutual information

The proper delay for attractor dimension specified in the patent

Spectral density as a function of frequency identifying the exponent of $1/f^\alpha$ behavior Other nonlinear chaotic measures Horizon for predictability better than statistical techniques as a function of length, frequency, attractor dimension and Lyapunov exponent or Kolmogorov entropy.

Figure 37:
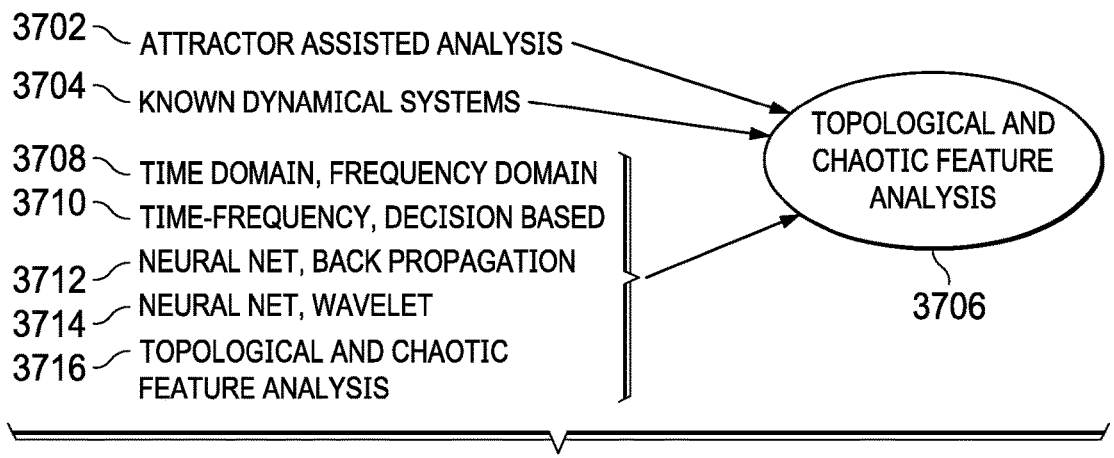
FIG. 37 illustrates traits utilized for performing topological and chaotic feature analysis.

As shown in FIG. 37, in addition to the attractor assisted analysis 3702 described above, known dynamical systems 3704 can further be used that may have similar dynamical features and model the system for PQ, QR, RS, ST and TU as well as PP, QQ, RR, SS, TT, UU signals. This modeling may allow us to do better biomechanical engineering as well as creating better models of heart behavior to provide for topological and chaotic feature analysis 3706.

Additional techniques can also combine the Time domain 3708, frequency domain 3710, time-frequency 3712, decision based neural net 3714, back propagation neural net 3716, wavelet 3718, as well as topological and chaotic feature analysis 3720 to increase accuracy (AC), sensitivity (SN), specificity (SP) and precision (P).

Catastrophe Features Analysis

Catastrophe theory is a way for a continuous function to model an abrupt change that would normally be called a discontinuity. The word catastrophe refers to an abrupt, discontinuous transition. The most typical function is single-valued everywhere except a region where it is sort of folded so that it has three values. As a point wanders over to where the function has more than one value, it tends to maintain continuity.

Chaos theory, formally called nonlinear dynamics, describes things like turbulence which look random but are actually not, and can be described deterministically. Usually there is a single parameter that, when increased, causes a nonlinear system to go from a simple oscillation to increasingly chaotic behavior. Table 1 illustrates the first seven Thom's catastrophes.

TABLE 1

| Name | Co-dimension | Co-rank | Universal unfolding |
|---|---|---|---|
| Fold | 1 | 1 | $x^3 + ux$ |
| Cusp | 2 | 1 | $x^4 + ux^2 + vx$ |
| Swallow tail | 3 | 1 | $x^5 + ux^3 + vx^2 + wx$ |
| Hyperbolic umbilic | 3 | 2 | $x^3 + y^3 + uxy + vx + wy$ |
| Elliptic umbilic | 3 | 2 | $x^3 - xy^2 + u(x^2 + y^2) + vx + wy$ |
| Butterfly | 4 | 1 | $x^6 + ux^4 + vx^3 + wx^2 + tx$ |
| Parabolic umbilic | 4 | 2 | $x^2 y + y^4 + ux^2 + vy^2 + wx + ty$ |

A combination of chaotic dynamics and catastrophe theory can model heart behavior and conditions for a heart attack. The use of chaotic dynamics and catastrophe theory can be combined with the other techniques described herein to model heart behavior and predict a potential occurrence of a unhealthy heart condition or heart attack.

Classical Features Analysis

In classical feature analysis some usual linear features in the time domain and the frequency domain are extracted from an ECG signal. These linear features include five features in the time domain and four features in the frequency domain.

Figure 38:
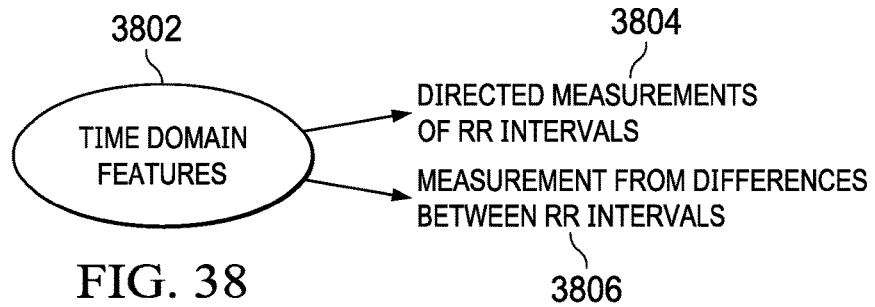
FIG. 38 illustrates various types of time domain features.

As shown in FIG. 38, the time-domain features 3802 include statistical time-domain measures that are divided into two classes, namely, direct measurements of RR intervals (or NN intervals) 3804 and measurements from the differences between RR intervals 3806. Direct measurements of RR intervals are features that include two simple time domain variables that can be calculated by a mean of all RR intervals (MNN), a standard deviation of all RR intervals (SDNN), measurements from the differences between RR intervals are determined using the square root of the mean of the squares of differences between adjacent RR Intervals (RMSSD) and the standard deviation of differences between adjacent RR intervals (SDSD).

Figure 39:
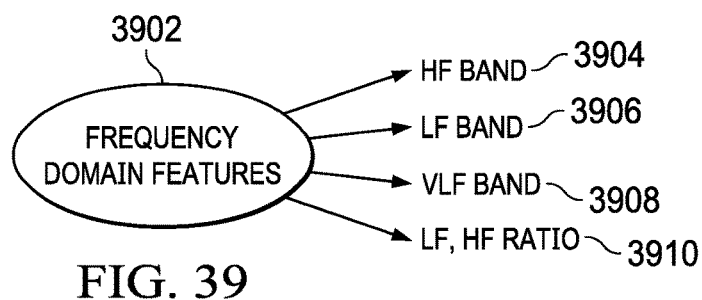
FIG. 39 illustrates various types of frequency domain features.
Figure 40:
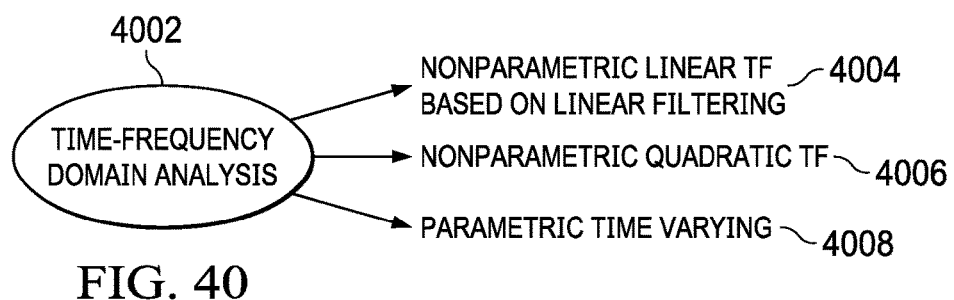
FIG. 40 illustrates various types of time-frequency domain analysis.

Referring now to FIG. 39, with respect to frequency domain features 3902, although the time domain parameters are computationally effective, they lack the ability to discriminate between the sympathetic and parasympathetic contents of the RR intervals. It is generally accepted that the spectral power in the high frequency (HF) band (0.15-0.4 Hz) 5904 of the RR intervals reflects the respiratory sinus arrhythmia (RSA) and thus cardiac vagal activity. On the other hand, the low frequency (LF) band (0.04-0.15 Hz) 5906, is related to the baroreceptor control and is mediated by both vagal and sympathetic systems. The LF 5906, HF 5904, and VLF (Very Low Frequency) bands 5908 power spectral density (PSD) and ratio of the LF and HF bands 5910 power spectral density (LF/HF) can be used as the frequency domain features of the RR interval signal.

Time-Frequency Domain Analysis

Another approach to analyze nonstationary HRV signal, is a time-frequency (TF) method 4002. This can be divided into three main categories: nonparametric linear TF methods based on linear filtering 4004, including the short-time Fourier transform and the wavelet transform, nonparametric quadratic TF representations 4006, including the Wigner distribution and its filtered versions, and parametric time-varying methods 4008 based on autoregressive models with time-varying coefficients. Smoothed Pseudo Wigner distribution provides better time frequency resolution than nonparametric linear methods. The main drawback of the technique is the presence of cross-terms, which should be suppressed by the time and frequency filtering.

Time-Frequency Features Extraction

Figure 41:
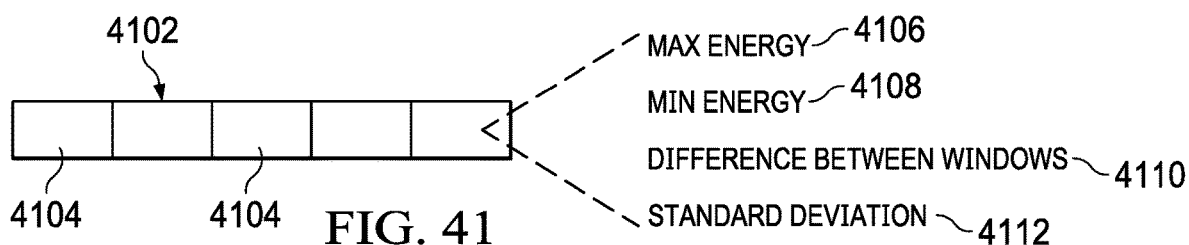
FIG. 41 illustrates an HRV signal.

As shown in FIG. 41, each HRV signal 4102 can be divided into five segments 4104 of equal length, each segment can be approximately 15 seconds in the time domain. The average energy of each segment 4104 can be computed. The features of the segments 4104 are: maximum amount of energy in each window 4106, minimum amount of energy in each window 4108, difference between maximum and minimum amount of energy between windows 4110, and standard deviation between energy of time windows 4112.

The obtained signal in time frequency domain is also divided into three frequency segments including the very low frequency band, the low frequency band and the high frequency band. Within each of the frequency bands the totally energy and the average energy for the segment can be determined in the following manners. The total energy of signal in the very low frequency band (0.003-0.04) Hz is divided by length of band (0.037). The total energy of signal in low frequency band (0.04-0.15) Hz is divided by length of band (0.11). The total energy of signal in high frequency band (0.15-0.4) Hz is divided by length of band (0.25). With respect to the average energy signal the average of energy signal in very low frequency band (0.04-0.003) Hz is determined, the average of energy signal in low frequency band (0.04-0.15) Hz is determined and the average of energy signal in high frequency band (0.15-0.4) Hz is determined.

Also, the first order derivative can be calculated as a feature to show the difference between adjacent windows. This derivative is the difference between the average energy in subsequent windows. The features in time span of 15 seconds can show that in a SCD person, the feature change from one window to next window is much more dominant so that we look for the first order derivative.

Nonlinear Analysis

Considering that a cardiovascular system has non-stationary behaviors and is more complex than a linear system, few Nonlinear Analyses can be used to show chaotic dynamical characteristics in HRV signal in addition to the time-frequency features. In this way, four different nonlinear parameters of the RR intervals can be extracted, which are described as below.

1. Poincare Plot

When in the RR intervals, each interval RR(n+1) is plotted as a function of previous interval RR(n), the resulting plot is known as the Poincare plot. A Poincare plot is a graphical representation of the correlation between the successive RR intervals. This plot can be quantitatively analyzed by calculating the standard deviations of the distances of the points. These standard deviations can be represented by SD1 and SD2, respectively. In fact, SD1 represents the fast beat-to-beat variability, while SD2 describes the relatively long-term variability in the HRV signal. The length (SD2) and the width (SD1) of the long and short axes of Poincare plot images represent short and long-term variability of any Nonlinear dynamic system. A mathematical relationship can be developed between each measure from the Poincare plot in order to understand existing heart rate variability indexes. A strong correlation may be found when comparing high frequency power of heart rate signals (modulated by parasympathetic nervous system) with SD1. SD2 can also be correlated with both low and high frequency power (modulated by both the parasympathetic and sympathetic nervous system). The ratio SD1/SD2 can be used to describe the relation between the two components.

2. DFA Analysis Method

Detrended fluctuation analysis (DFA) is a method for quantifying long-range correlations embedded in a seemingly non-stationary time series, and avoids the spurious detection of apparent long-range correlations that are artifacts of non-stationarity. This method is a modified root mean square analysis of a random walk.

Feature Selection

Figure 42:
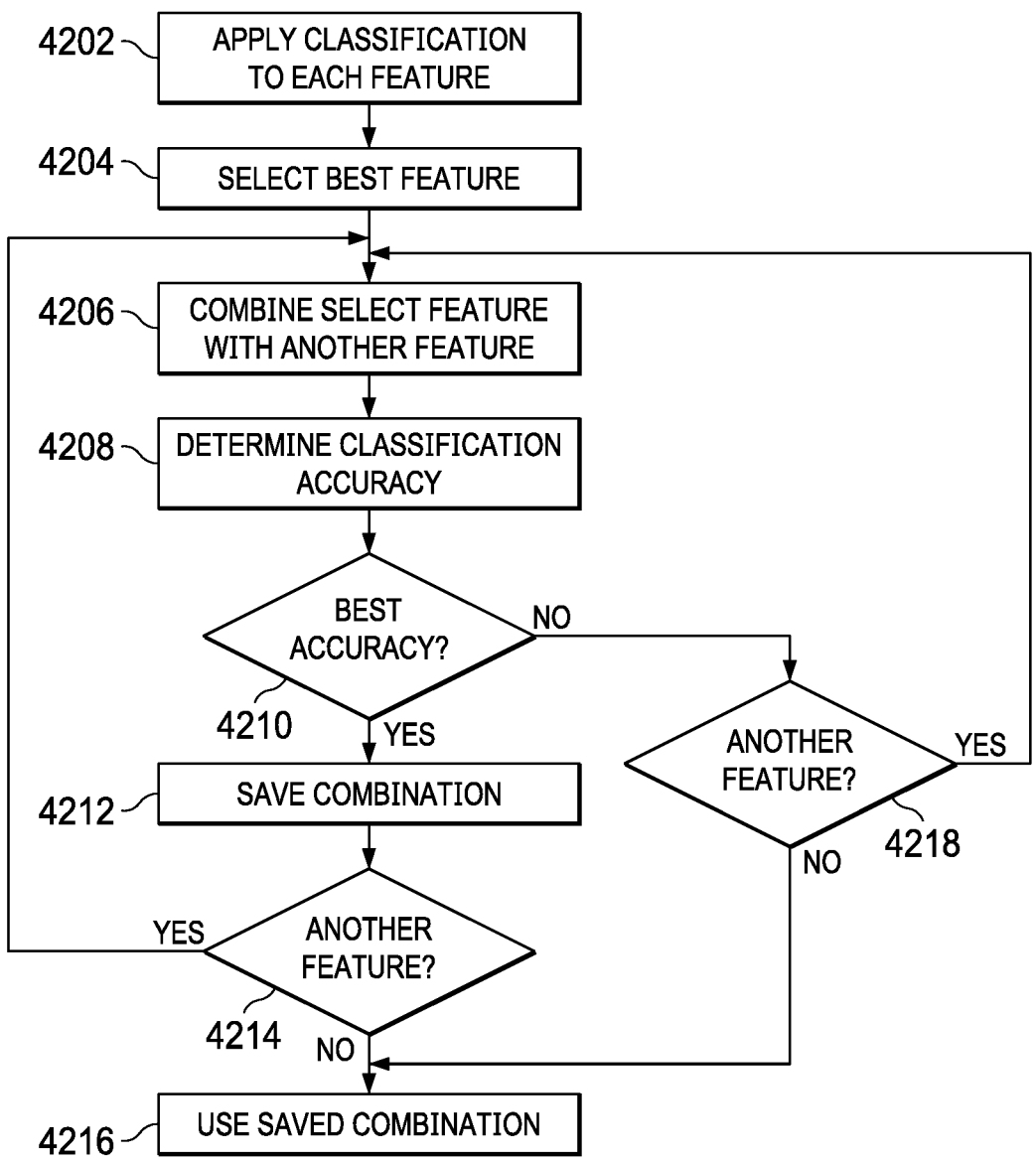
FIG. 42 illustrates a flow diagram of a process for combining heart signal features for analysis.

Using the obtained features from Linear, Time-Frequency and Nonlinear Processing and constituting a new combinational feature brings a good separability between two classes (i.e., Healthy people and People at risk of SCD). But in any classification task, there is a possibility that some of the extracted features might be redundant. These features can increase the cost and running time of the algorithms and decrease its generalization performance. In this way, the selection of the best discriminative features plays an important role when constructing classifiers. Referring now to FIG. 42 there is described the process for identifying the best features (for classification) in feature space. First, the classification can be applied at step 4202 separately to each feature. The best feature can be selected at step 4204 in accordance with the most value of classification accuracy. This feature can be combined with the other individual features and thus the best pair combination can be produced. The selected feature is combined with one of the other features at step 4206. The classification accuracy of the combination is determined at step 4208. Inquiry step 4210 determines if the combination provides the best classification accuracy. If so, the combination is saved at step 4212. Inquiry step 4214 then determines if further features exist for combining with the selected feature. If so, control passes back to step 2306 to combine the other feature with the selected feature and the process proceeds as before. If inquiry step 4210 determines that the new combination does not provide a better classification accuracy, control passes to inquiry step 4218 to determine if another feature for combination exists. If another feature exists, control passes back to step 4206. When inquiry steps 4214 and 4218 determine that no further features exist for a combination, the saved combination of features is used. This same process can then be repeated to add a third feature to a best combination of two features and so forth until an optimum number of features are determined. The optimal feature space can be achieved when the minimum number of features results in the highest classification accuracy. This process of adding additional features to combinations of one or more features can be stopped when adding a new feature decreases the classification accuracy of a combination or does not result in an increase. Each time this process is run, a different optimal combination of features can be obtained using a different training and test data.

Classification

Figure 43:
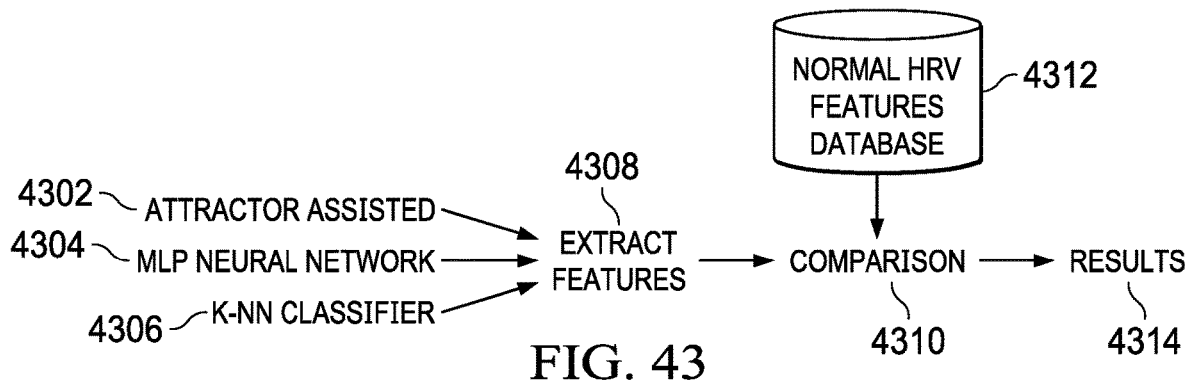
FIG. 43 illustrates a further process for analyzing a heart rate signal.

Referring now to FIG. 43, to discriminate between ECG of normal person and a person who is prone to sudden cardiac death, the system can use Attractor Assisted technique 4302, the Multilayer perceptron (MLP) neural network 4304 and K-Nearest Neighbor (k-NN) classifier. Features 4306 extracted from HRVs of one-minute intervals at 4308 (i.e., the first one minute, the second one minute, the third one minute and the fourth one minute before SCD) can be compared at 4310 with normal HRVs of one minute from a Normal HRV feature database 4312 to generate a result 4314 that indicates whether the monitored HRV features correspond to a normal person or a person prone to sudden cardiac death.

Multilayer Perceptron Neural Network

Figure 44:
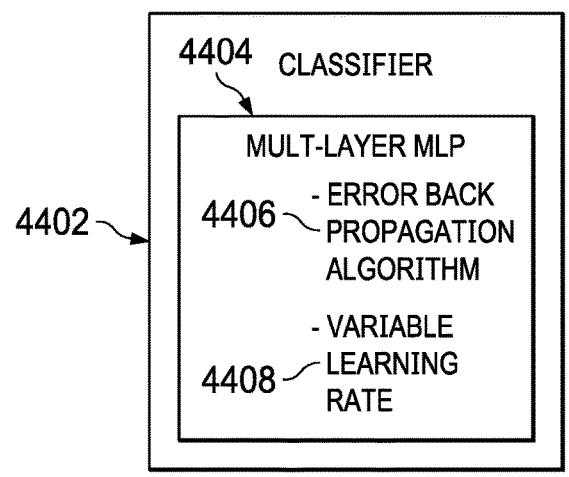
FIG. 44 illustrates a block diagram of a classifier.

As shown in FIG. 44, a classifier 4402 can be built using a Multi-layer MLP 4304 with error back propagation algorithm 4406 and variable learning rate 4408. All the possible combinations of the selected numbers of neurons in the hidden layer can be selected, trained and finally optimized for the number of layers and neurons in each layer. The output nodes have linear transfer functions, and the hidden layer can use the usual sigmoid function. Network training can continue until the mean square error became less than a specified threshold or the number of training iterations reached a specified number.

k-Nearest Neighbor

The k-nearest neighbor algorithm 4306 is a non-parametric method for classifying objects based on closest training examples in the feature space. It is a type of instance-based learning where the function is only approximated locally, and all computation is deferred until classification. The k-nearest neighbor algorithm 4306 is amongst the simplest of all machine learning algorithms. An object is classified by a majority vote of its neighbors, with the object being assigned to the class most common amongst its k nearest neighbors (k is a positive integer, typically small). Over several distance measures that might be used in this algorithm, Euclidean distance can be used as the distance measure. If k=1, then the object is simply assigned to the class of its nearest neighbor. The selected feature set is then used to determine the best value of k for the classifier. Therefore, different numbers of nearest neighbors (k=1, 3, 5, 7, 9) can be tested in the classifier with respect to computational time to obtain the best performance for the classifier. Performances of all classifiers can be calculated based on their accuracy.

Evaluation

The ability of the proposed method for prediction of sudden cardiac death is evaluated using accuracy (AC), sensitivity (SN), specificity (SP) and precision (P). If TP refers to true positives (correctly predicted SCD), TN refer to true negatives (correctly predicted non-SCD), FN refer to false negatives (incorrectly predicted non-SCD) and FP refer to false positives (incorrectly predicted SCD). These terms can be evaluated in the following manner.

Accuracy (AC): proportion of correct predictions to the total predictions $$AC=(TP+TN)/(TP+TN+FN+FP)$$

Sensitivity (SN): proportion of true positives to the total positives $$SN=TP/(FN+TP)$$

Specificity (SP): proportion of true negatives to the total negatives $$SP=TN/(TN+FP)$$

Precision (P): proportion of predicted positive cases that were correct $$P=TP/(FP+TP)$$

To evaluate the method, AC, SN, SP and P are computed for MLP classifier 4402 for one, two, three and four minutes before SCD (to evaluate the robustness of the approach, this procedure must be repeated for multiple times).

Figure 45:
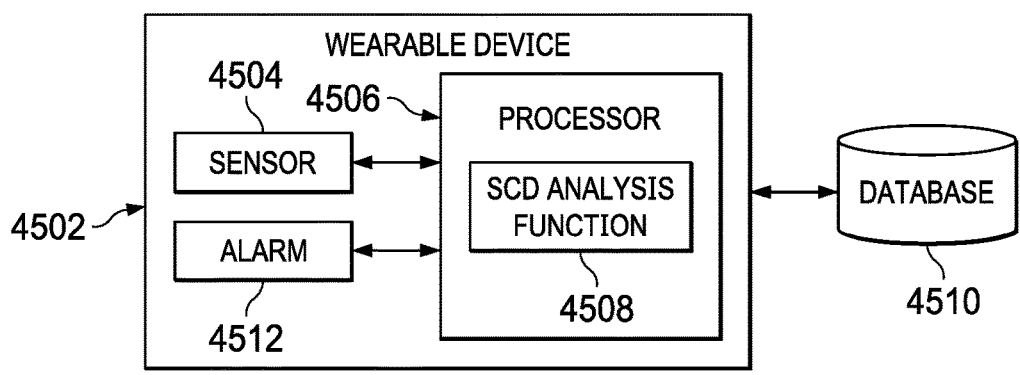
FIG. 45 illustrates a block diagram of a wearable device system for analyzing heart signals to determine sudden cardiac death symptoms.
Figure 46:
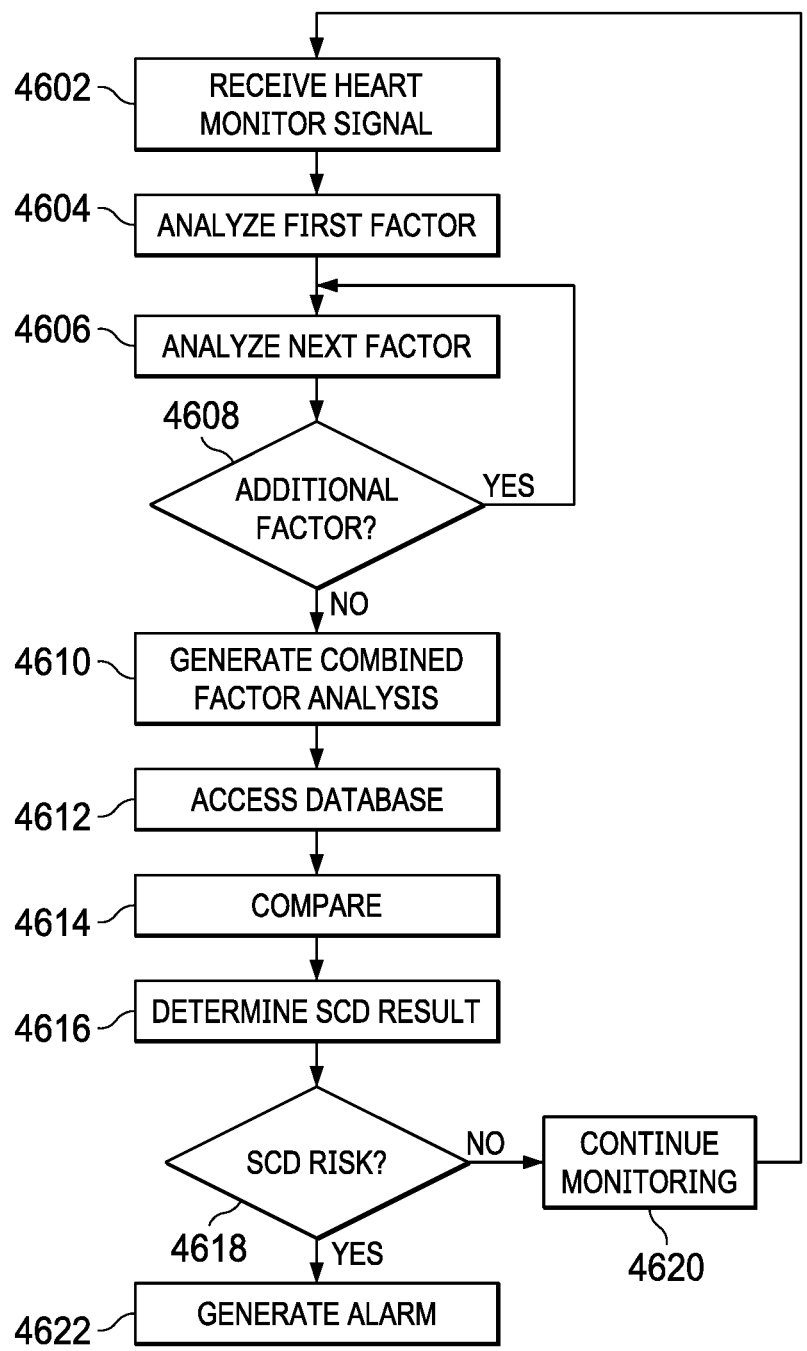
FIG. 46 illustrates a flow diagram of a process for locating sudden cardiac death symptoms from a monitored heart signal.

Referring now to FIGS. 45 and 46, there are more particularly illustrated the system and method for using a wearable device for monitoring for SCD events. As shown in FIG. 45, a wearable device 4502, for example an Apple® watch, may monitor an individual's heart beat using a sensor 4504 incorporated within the wearable device 4502 to generate an ECG signal. These generated ECG signals are analyzed using a processor 4506 that implements an SCD analysis function 3960 that implements some or all of the various analysis processes described hereinabove for analyzing the received ECG signals to monitor for potential SCD events. The SCD analysis function 4508 accesses a database 4510 which may be located remotely from the wearable device 4502, or alternatively, can be located within a memory of the wearable device 4502. The analysis performed by the SCD analysis function 4508 will generate an alarm signal to an alarm 4512 when potential SCD conditions exist within an individual wearing the wearable device 4502 to notify them to seek medical treatment.

FIG. 46 illustrates a flow diagram of the process performed by the system illustrated in FIG. 45. The sensor 4504 receives the heart monitoring signals from a wearer of the wearable device 4502 at step 2702. The SCD analysis function 4508 analyzes a first feature at step 4604 associated with the received heart monitor signal. The feature analyzed by the SCD analysis function 4508 may comprise any of those described hereinabove, including, but not limited to, time-bandwidth, nonlinear features, topological features, dynamical invariants, catastrophe theory, time domain, frequency domains, time frequency, decision based neural net, back relegation neural net, wavelets as well as topological and chaotic feature analysis. After the first feature is analyzed at step 4604, a next feature is analyzed at step 706 that again may comprise any of the above referenced manners of analysis.

Inquiry step 4608 determines if additional features are available for analysis and if so control proceeds back to step 4606 two provide analysis of the additional feature. If inquiry step 4608 determines that additional features are not available, control passes to step 4610 where a combined feature analysis is made based upon each of the analyzed features to provide a kind result with respect to the ECG signal. The database 4510 may then be accessed to obtain results for comparison to the results generated by the SCD analysis function 4508. The feature results within the database 4510 will represent normal patients and patients likely to suffer an SCD event. The results from the database are compared to the generated combined feature analysis at step 4614 such that a determination of the potential for an SCD result may be made at step 4616. Inquiry step 4618 determines if there exists a risk of an SCD and if not, control passes to step 4622 can you and you monitoring for new heart signals. If inquiry step 4618 determines that there exists an SCD risk an alarm is generated at step 4622 using the alarm 4512.

Although there is not a significant difference between normal ECG and those patients which prone to SCD, by using the proposed combination of features, symptoms of SCD can be observed before the SCD. Today Cardiology and Electrocardiography experts cannot distinguish between normal ECG and patients who are prone to SCD, however the proposed extracted features can be used to predict SCD.

It will be appreciated by those skilled in the art having the benefit of this disclosure that this of a system for using topological features and time bandwidth signature of heart signals as biomarkers to detect deterioration of a heart provides an improved method for monitoring a heart signal to predict sudden cardiac death in conditions. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A system for monitoring an individual for conditions indicating a possibility of occurrence of irregular heart events, comprising:
  a database including a plurality of combinations of at least a first signature and a second signature, wherein the first signature comprises time-bandwidth product features and the second signature comprise topological features, a first portion of the plurality of combinations associated with a normal heartbeat and a second portion of the plurality of combinations associated with an irregular heart event;
  a wearable heart monitor that is worn on a body of a patient, comprising:
    a heart sensor for generating a heart signal responsive to monitoring a beating of a heart of the individual;
    a processor for receiving the heart signal from the heart sensor, wherein the processor is configure to analyze the heart signal using a plurality of different processes, each of the plurality of different processes generating at least one of the first signature comprising the time-bandwidth product features and the second signature comprising the topological features, the plurality of different processes providing a unique combination including at least the first signature and the second signature for the generated heart signal; and
    wherein the processor compares the unique combination with the plurality of combinations in the database, locates a combination of the plurality of combinations within the database that substantially matches the unique combination and generates a first indication if the unique combination substantially matches one of the first portion of the plurality of combinations and a second indication if the unique combination substantially matches one of the second portion of the plurality of combinations.

2. The system of claim 1 further including an alarm for generating an alarm indication responsive to generation of the second indication.

3. The system of claim 1, wherein the database is located within the wearable heart monitor.

4. The system of claim 1, further comprising additional signatures comprising features of the heart signal, the features of the heart signal comprising at least one feature from the group consisting of, non-linear features and dynamical invariants.

5. The system of claim 1, further comprising additional signatures comprising features of the heart signal, the features of the heart signal comprising at least one feature from the group consisting of, chaotic features, catastrophe features, time domain features, frequency domain features, time-frequency domain features, and non-linear features.

6. The system of claim 5, wherein the topological features and the chaotic features comprise at least one of embedded dimensions of an attractor, fractional attractor dimensions, Correlation dimensions, Lyapunov exponent, Kolmogorov Entropy, Mutual Information, a proper delay for an attractor dimension, spectral density as a function of frequency, nonlinear chaotic measures, and a horizon for predictability.

7. The system of claim 5, wherein the time domain features comprise at least one of direct measurement of RR intervals, measurements of differences between RR intervals, a mean of all RR intervals, a standard deviation of all RR intervals, a square root of a mean of squares of differences between adjacent RR intervals and standard deviation of differences between adjacent RR intervals.

8. The system of claim 5, wherein the frequency domain features comprise low frequency band power spectral density features, high frequency band power spectral density features, very low frequency band power spectral density features, and ratio of low frequency band and high frequency band power spectral density.

9. The system of claim 5, wherein the time-frequency domain features comprise maximum amount of energy in a time window, minimum amount of energy in the time window, difference between maximum and minimum amount of energy between time windows, standard deviation between energy of time windows, total energy of a signal in a low frequency band, total energy of a signal in a high frequency band, average energy of a signal in a very low frequency band, average energy of a signal in a low frequency band, and average energy of a signal in a high frequency band.

10. The system of claim 5, wherein the non-linear features comprise at least one of a Poincare plot of a correlation between successive RR intervals in the heart signal and quantified long-range correlations generated by Detrended Fluctuation Analysis.

11. The system of claim 1, where the processor selects an optimal number of features comprising at least two features to provide a best classification accuracy for a combination of at least the first signature and the second signature.

12. The system of claim 11 further including a multilayer perceptron neural network for selecting the optimal number of features.

13. The system of claim 11, wherein the processor implements a k-nearest neighbor algorithm for selecting the optimal number of features.

14. A method for monitoring an individual for conditions indicating a possibility of occurrence of irregular heart events, comprising:
storing a plurality of combinations of at least a first signature and a second signature, wherein the first signature comprises time-bandwidth product features and the second signature comprise topological features, a first portion of the plurality of combinations associate with a normal heartbeat and a second portion of the plurality of combinations associated with an irregular heart event;
generating a heart signal using a heart sensor within a wearable heart monitor responsive to monitoring a beating of a heart of the individual;
receiving the heart signal from the heart sensor at a processor;
analyzing the heart signal at the processor using a plurality of different processes;
generating at least one of the first signature comprising the time-bandwidth product features and the second signature comprising the topological features from at least two of the plurality of different processes, the at least two of the plurality of different processes providing a unique combination including at least the first signature and the second signature for the generated heart signal;
comparing the unique combination with the plurality of combinations in a database;
locating a combination of the plurality of combinations within the database that substantially matches the unique combination; and
generating a first indication if the unique combination substantially matches one of the first portion of the plurality of combinations and a second indication if the unique combination substantially matches one of the second portion of the plurality of combinations.

15. The method of claim 14 further including generating an alarm indication responsive to generation of the second indication.

16. The method of claim 14, further comprising additional signatures comprising features of the heart signal, the features of the heart signal comprising at least one feature from the group consisting of chaotic features, catastrophe features, time domain features, frequency domain features, time-frequency domain features, and non-linear features.

17. The method of claim 16, wherein the topological features and the chaotic features comprise at least one of embedded dimensions of an attractor, fractional attractor dimensions, Correlation dimensions, Lyapunov exponent, Kolmogorov Entropy, Mutual Information, a proper delay for an attractor dimension, spectral density as a function of frequency, nonlinear chaotic measures, and a horizon for predictability.

18. The method of claim 16, wherein the time domain features comprise at least one of direct measurement of RR intervals, measurements of differences between RR intervals, a mean of all RR intervals, a standard deviation of all RR intervals, a square root of a mean of squares of differences between adjacent RR intervals and standard deviation of differences between adjacent RR intervals.

19. The method of claim 16, wherein the frequency domain features comprise low frequency band power spectral density features, high frequency band power spectral density features, very low frequency band power spectral density features, and ratio of low frequency band and high frequency band power spectral density.

20. The method of claim 16, wherein the time-frequency domain features comprise maximum amount of energy in a time window, minimum amount of energy in the time window, difference between maximum and minimum amount of energy between time windows, standard deviation between energy of time windows, total energy of a signal in a low frequency band, total energy of a signal in a high frequency band, average energy of a signal in a very low frequency band, average energy of a signal in a low frequency band, and average energy of a signal in a high frequency band.

21. The method of claim 16, wherein the non-linear features comprise at least one of a Poincare plot of a correlation between successive RR intervals in the heart signal and quantified long-range correlations generated by Detrended Fluctuation Analysis.

22. The method of claim 14 further comprising selecting an optimal number of features comprising at least two features to provide a best classification accuracy for a combination of at least the first signature and the second signature.

23. The method of claim 22, wherein the step of selecting further comprises selecting the optimal number of features using a k-nearest neighbor algorithm.

24. A system for monitoring an individual for conditions indicating a possibility of occurrence of sudden cardiac death, comprising:
  a database including a plurality of combinations of at least a first signature and a second signature, wherein the first signature comprises time-bandwidth product features and the second signature comprise topological features, a first portion of the plurality of combinations associated with a normal heartbeat and a second portion of the plurality of combinations associated with an indication of a possibility of sudden cardiac death;
  a wearable heart monitor that is worn on a body of a patient, comprising:
    a heart sensor for generating a heart signal responsive to monitoring a beating of a heart of the individual;
    a processor for receiving the heart signal from the heart sensor, wherein the processor is configure to analyze the heart signal using a plurality of different processes, each of the plurality of different processes generating at least one of the first signature and the second signature, the plurality of different processes providing a unique combination including at least the first signature and the second signature for the generated heart signal, the first signature comprising a time-bandwidth product feature and the second signature comprising topological features;
    wherein the processor compares the unique combination with the plurality of combinations in the database, locates a combination of the plurality of combinations within the database that substantially matches the unique combination and generates a first indication if the unique combination substantially matches one of the first portion of the plurality of combinations and a second indication if the unique combination substantially matches one of the second portion of the plurality of combinations; and
    an alarm for generating an alarm indication responsive to generation of the second indication.

25. The system of claim 24, wherein the database is located within the wearable heart monitor.

26. The system of claim 24, where the processor selects an optimal number of features comprising at least two features to provide a best classification accuracy for a combination of at least the first signature and the second signature.

27. The system of claim 26 further including a multilayer perceptron neural network for selecting the optimal number of features.

28. The system of claim 26, wherein the processor implements a k-nearest neighbor algorithm for selecting the optimal number of features.

* * * * *